(12) United States Patent
Rodriguez-Cabello et al.

(10) Patent No.: US 9,932,369 B2
(45) Date of Patent: Apr. 3, 2018

(54) THERMOSENSITIVE, BIOACTIVE BIOPOLYMER AND ASSOCIATED METHOD OF CELL HARVESTING

(75) Inventors: Jose Carlos Rodriguez-Cabello, Valladolid (ES); Francisco Javier Arias Vallejo, Valladolid (ES); Matilde Alonso Rodrigo, Valladolid (ES); Mercedes Santos Garcia, Valladolid (ES); Maria Pierna Alvarez, Valladolid (ES)

(73) Assignee: UNIVERSIDAD DE VALLADOLID, Valladolid (ES)

( * ) Notice: Subject to any disclaimer, the term of this patent is extended or adjusted under 35 U.S.C. 154(b) by 660 days.

(21) Appl. No.: 14/123,989

(22) PCT Filed: Jun. 8, 2012

(86) PCT No.: PCT/ES2012/070431
§ 371 (c)(1),
(2), (4) Date: Apr. 11, 2014

(87) PCT Pub. No.: WO2012/168532
PCT Pub. Date: Dec. 13, 2012

(65) Prior Publication Data
US 2014/0227782 A1 Aug. 14, 2014

(30) Foreign Application Priority Data
Jun. 9, 2011 (ES) .................................. 201130962

(51) Int. Cl.
*A61K 38/00* (2006.01)
*C12N 5/00* (2006.01)
*C07K 1/00* (2006.01)
*C07K 14/00* (2006.01)
*C07K 17/00* (2006.01)
*C07H 21/02* (2006.01)
*C07H 21/04* (2006.01)
*A61L 27/34* (2006.01)
*C07K 14/78* (2006.01)
*C08L 89/00* (2006.01)
*A61L 27/22* (2006.01)
*A61L 27/38* (2006.01)
*A61L 27/50* (2006.01)

(52) U.S. Cl.
CPC .......... *C07K 14/001* (2013.01); *A61L 27/227* (2013.01); *A61L 27/34* (2013.01); *A61L 27/38* (2013.01); *A61L 27/50* (2013.01); *C07K 14/78* (2013.01); *C08L 89/00* (2013.01)

(58) Field of Classification Search
None
See application file for complete search history.

(56) References Cited

U.S. PATENT DOCUMENTS

2010/0189643 A1* 7/2010 Chilkoti ............... A61K 51/088
424/1.65

FOREIGN PATENT DOCUMENTS

| EP | 1 748 064 A1 | 1/2007 |
| JP | 2001340076 A | 12/2001 |
| JP | 2007518811 A | 7/2007 |
| JP | 2010521246 A | 6/2010 |
| WO | 2005/028639 A2 | 3/2005 |
| WO | 2007112048 A2 | 10/2007 |
| WO | 2010092224 A1 | 8/2010 |
| WO | 2011/036326 A2 | 3/2011 |

OTHER PUBLICATIONS

Srivastava et al. "Elastin-like recombinamers as substrates for retinal pigment epithelial cell growth" J. Biomed. Mater. Res. Part A: 97A:243-250. Published Mar. 25, 2011.*
Ozturk et al., Dynamic cell culturing and its application to micropatterned, elastin-like protein-modified poly (N-isopropylamide) scaffolds, Biomaterials, vol. 30, No. 29, pp. 5417-5427, Oct. 1, 2009.
Oliveira et al., Development of an injectable system based on elastin-like recombinamer particles for tissue engineering applications, Soft Matter, vol. 7, No. 14, pp. 6426-6434, Apr. 4, 2011.
EPO, Supplemental European Search Report dated Feb. 11, 2015 issued in corresponding European Patent Application No. 12796308.
Zhang, H., et al., "Human amniotic cell sheet harvest using a novel temperature-responsive culture surface coated with protein-based polymer", Tissue Engineering, vol. 12, No. 2, Feb. 1, 2006 (Feb. 1, 2006), pp. 391-402, Larchmont, NY.
Ribeiro, A., et al., "Influence of the amino acid sequence on the inverse temperature transition of elastin-like polymers", Biophysical Journal, vol. 97, Jul. 2009 (Jul. 2009), pp. 312-320, Cell Press.
Javier Arias, F., et al., "Tailored recombinant elastin-like polymers for advanced biomedical and (nano) biotechnological applications", Biotechnology Letters, vol. 28, 2006, pp. 687-695, Springer Netherlands.
JPO, Decision of Refusal dated Oct. 18, 2016 issued in corresponding Japanese Patent Application No. 2014-514116.
Costa, R., et al., "Stimuli-responsive thin coatings using elastin-like polymers for biomedical applications", Advanced Functional Materials, 2009, vol. 19, pp. 3210-3218.

(Continued)

*Primary Examiner* — Christina Bradley
*Assistant Examiner* — Zachary J Miknis
(74) *Attorney, Agent, or Firm* — Gottlieb, Rackman & Reisman, P.C.

(57) ABSTRACT

The present invention relates to a biopolymer and a cell-harvesting scaffold comprising same, as well as the associated cell-harvesting method that allows said harvesting to be performed in a simple and effective manner by reducing the culture temperature. The present invention also relates to a method for synthesizing said biopolymer.

11 Claims, 14 Drawing Sheets

(56) References Cited

OTHER PUBLICATIONS

Kurihara, H., et al., "Recombinant extracellular matrix-like proteins with repetitive elastin or collagen-like functional motifs", Biotechnology Letters, 2005, vol. 27, pp. 665-670.

Kaufmann, D., et. al., "Chemical conjugation of linear and cyclic RGD moieties to a recombinant elastin-mimetic polypeptide-A versatile approach toward bioactive protein hydrogels", Macromolecular Bioscience, 2008, vol. 8, pp. 577-588.

Luan. C., et. al., "Solvent deuteration enhancement of hydrophobicity: DSC study of the inverse temperature transition of elastin-based polypeptides", Journal of Physical Chemistry, 1991, vol. 95 (20), pp. 7896-7900.

Yamaoka, T., et. al., "Mechanism for the phase transition of a genetically engineered elastin model peptide (VPGIG)40 in aqueous solution", Biomacromolecules, 2003, vol. 4, pp. 1680-1685.

Banta, et al., "Protein engineering in the development of functional hydrogels", Annual Review of Biomedical Engineering, 2010, vol. 12, pp. 167-186.

\* cited by examiner

FIG. 1
FIG. 2
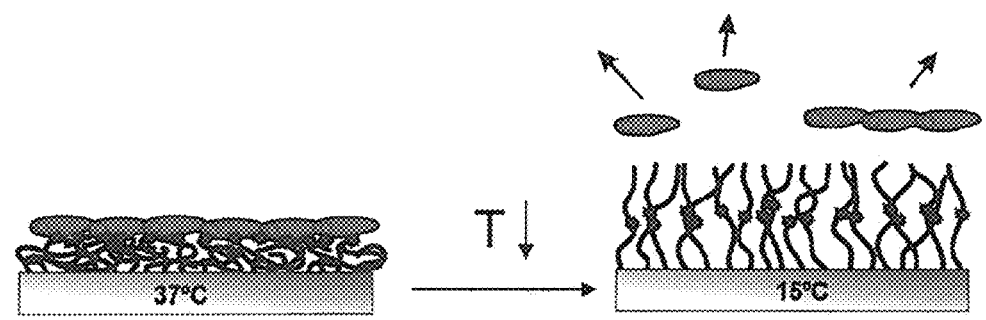
FIG. 3
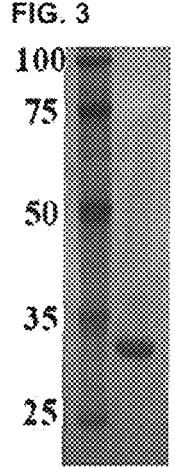

THERMOSENSITIVE, BIOACTIVE BIOPOLYMER AND ASSOCIATED METHOD OF CELL HARVESTING

SEQUENCE LISTING

The instant application contains a Sequence Listing which has been submitted in ASCII format via EFS-Web and is hereby incorporated by reference in its entirety. Said ASCII copy, created on Mar. 21, 2014, is named Listado de Secuencias.txt_es-ES_en-Gb.TXT, and is 28 kilobytes in size.

The present invention belongs to the field of tissue engineering and relates to a biopolymer and cell-harvesting scaffold comprising said biopolymer that allows cell harvesting in a simple and efficient manner. The cells bound to the scaffold are released by way of a simple temperature change, preserving the cell surface proteins and maintaining high cell viability. Moreover, the surface may present selectivity for various cell lines either globally or locally and does not release residues into the tissue generated as the temperature-sensitive biopolymer is covalently bound to the scaffold.

PRIOR ART

In the field of tissue engineering, the combination of various materials with live cells provides a novel and interesting means of undertaking regenerative therapies. Surfaces may be functionalised to provide them with adherent or anti-adherent properties, specific groups that promote interactions between the material and cells, smart behaviour (sensitivity to stimuli) or micro- or nanopatterns.

Both smart surfaces and drug-release systems, artificial organs and systems for regenerative medicine are normally developed using new biofunctional materials with properties of marked interest in the field of biomedical research, said materials being sensitive to different stimuli. More specifically, materials sensitive to a wide range of stimuli, such as light, temperature, pH, ionic strength or electric fields, are available for such applications. A specific stimulus may modify the state or configuration of various biomolecules, thereby altering the affinity thereof for a specific surface and, consequently, preventing the adsorption thereof (Hyun, J. et al. 2004 *Journal of the American Chemical Society*. 126, 7330-7335). In other words, such systems respond to stimuli.

The temperature-sensitive surfaces obtained from certain materials undergo a change in molecular conformation in response to temperature changes in the environment. Some polymers exhibit the opposite behaviour in response to temperature. Such polymers become less solvated as the temperature increases and precipitate from solution at a temperature known as the "lower critical solution temperature" (LCST). The polymers that respond to these characteristics used in bio-applications include N-alkyl-substituted polyacrylamides, polyalcohols or polypeptides. The latter may be natural or produced using genetic-engineering techniques and, consequently, possess high levels of specificity, contain specific groups for a large number of applications and even be biodegradable. Elastin-like polymers (ELPs) are an excellent example of such polypeptides (Cole, M. A. et al. 2009 *Biomaterials*. 30, 1827-50).

The growth and release of cells, more specifically cell sheets, is one of the most widely studied and most interesting biomedical applications in which temperature-sensitive smart surfaces are used.

The most common and widely studied model for such temperature-sensitive systems is probably poly(N-isopropylacrylamide) (PIPAAm), which was developed by Okano. PIPAAm exhibits an LCST of 32° C. in aqueous solution. Below said temperature PIPAAm is fully hydrated in aqueous solution, with an extended conformation, whereas above the LCST it is dehydrated and compacted. Thus, PIPAAm surfaces allow molecular interactions to be modulated on the basis of temperature, and numerous reversible, temperature-dependent adhesion/detachment studies of proteins and bacterial and mammalian cells can be found (Cole, M. A. et al. 2009 *Biomaterials*. 30, 1827-50).

Various polymers with temperature-responsive properties similar to those of PIPAAm, which allow culture of a wide range of cells by adopting a collapsed state above a transition temperature (37° C.), are known. A decrease in temperature to below the critical temperature for the polymer causes said polymer to unfold and begin to release live cells or, if said cells have achieved confluence, an intact cell sheet. This, it is possible to rapidly harvest individual cells or intact cell sheets simply by decreasing the temperature (Kikuchi, A et al. 1998. *Journal of Biomaterials Science-Polymer Edition*. 9, 1331-1348).

Cell release from surfaces involves both a reduction in the interactions between the cells and the surface as a result of spontaneous hydration of the polymer chains bound to said surface and an active change in cell morphology and metabolic activity. Consequently, as a result of a simple temperature change, such temperature-sensitive polymers allow confluent cultures of a large number of cell types to be harvested as a cell layer similar to what could be a tissue, while maintaining inter-cell interactions and those between cells and the proteins in the extracellular matrix (Kushida, A., et al. 1999. *Journal of Biomedical Materials Research*. 45, 355-362).

The removal of cells from culture has always required aggressive enzymatic or mechanical methods that have a detrimental effect on the morphology of the cells being harvested. Such morphological changes have recently been ascribed to alterations to the cell membrane and glycocalyx, and often result in a loss of cell activity. It has been shown that such changes also affect the extracellular matrix, which is essential for cell adhesion, proliferation and differentiation, thereby having important implications during cell culture. It has been demonstrated that the method for detaching cells by way of a temperature decrease is much less destructive as regards obtaining a cell monolayer. Moreover, said method has a much lesser effect on the extracellular matrix in comparison with other, more traditional methods and techniques. Indeed, cells sheets apparently free from any damage to the extracellular matrix can be obtained (Canavan, H. E., et al. 2005. *J Biomed Mater Res A*. 75, 1-13). Said technique has been successfully applied to a wide range of cell types, including smooth muscle cells, hepatocytes, endothelial cells, fibroblasts, keratinocytes, epithelial cells, macrophages, microglial cells and stem cells.

Using cell sheets harvested from PIPAAm-functionalised surfaces, Okano et al. have established what is known as cell-sheet engineering to create multilayers of functional tissues in order to treat a broad range of diseases, such as corneal dysfunction, oesophageal cancer, tracheal resection and heart problems. More recently, a three-dimensional tissue comprising the cells and the highly vascularised deposited extracellular matrix thereof to obtain systems resembling organs such as the heart and liver (Yang, J. et al. 2007 *Biomaterials*. 28, 5033-43).

A further breakthrough in this field has been the joint culture of different cell types on the same surface. For example, surfaces coated with two different temperature-sensitive polymers, with different transition temperatures and cell-adhesion sequences, thereby allowing control of the system (Tsuda, Y. et al. 2005 Biomaterials. 26, 1885-93).

Other strategies have involved the immobilisation of peptides that promote cell adhesion, such as RGD (Ozturk, N. et al. 2009. Biomaterials, 30, 5417-26), growth factors such as insulin, epidermal growth factors or temperature-sensitive ELPs with adhesive properties (Hatakeyama, H. et al. 2006 Biomaterials. 27, 5069-78) to promote cell binding and communication between the cells and the material on the smart surfaces (Ebara, M. et al. 2008 Advanced Materials 20, 3034-3038; Mie, M. et al. 2008 J Biomed Mater Res B Appl Biomater. 86, 283-90). This approach shows the potential of such systems in the field of tissue engineering, as no additional growth factors are required. Moreover, different cell types can be selected and separated by using specific cell-adhesion domains, for example endothelial cells using the REDV domain (Girotti, A., et al. 2004 J. Mater. Sci.: Mater. Med. 15, 479-484). In this manner, polypeptides, either natural or synthesised using genetic-engineering techniques via recombinant DNA technology available for synthesising repetitive genes (Rodriguez-Cabello J. C. et al. 2010 J. Mater. Sci.: Mater. Med. 15(4): 479-84; Macewan, S. R. et al. 2010 Biopolymers 94(1): 60-77), have shown enormous potential in biomedical applications as such peptides can be produced with high levels of specificity, containing functional groups with cell-adhesion domains, cross-linking domains for covalent bonding to the surface and/or domains that can be recognised by more or less specific proteases that make such polypeptides biodegradable. Thus, a single polymer may contain different domains while conserving a smart response to temperature. ELPs are some of the best examples of such polymers. For example, Na et al. have created cell-based biochips by making use of the advantage provided by the rapid response of a smart material to external stimuli to create surfaces by ELP adsorption. The smart transition of ELPs means that when such compounds are bound to a glass surface, said surface changes from a hydrophobic to a hydrophilic state, and vice versa, depending on the temperature, thus allowing reversible cell adhesion control by way of the incubation temperature (Na, K. et al. 2008 Langmuir. 24, 4917-23; Rodrfguez-Cabello, J. C. et al. 2010 Advances in Biochemical Engineering/Biotechnology, 1-35).

In addition, it has been shown that it is possible to detach individual cells or cell sheets using polyvinylidene difluoride (PVDF) membranes by way of a small and simple temperature decrease and transfer said cells and sheets to a new surface to create cell-based multilayers, thereby suggesting the enormous potential of such an approach (Zhang, H. et al. 2006 Tissue Eng. 12, 391-401).

Continuing with this idea, Mie et al. have used genetic techniques to develop a new extracellular matrix containing two ELPs with different functionalities (polyhistidine tail and RGD sequence) for harvesting a cell sheet from a culture plate by lowering the temperature (Mie, M. et al. 2008 J Biomed Mater Res B Appl Biomater. 86, 283-90).

Consequently, ELPs are excellent candidates for cell harvesting due to the smart character with respect to temperature, biocompatibility and ability to incorporate cell-adhesion, cross-linking or biodegradability domains in the sequence thereof, thereby providing great potential in biomedical applications.

Moreover, such systems are suitable for non-mechanical and trypsin-free cell harvesting, thereby avoiding the drawbacks inherent to such procedures, such as the need for extensive experience and the damage caused to proteins on the cell surface, with the subsequent decrease in cell viability.

DESCRIPTION OF THE INVENTION

The present invention relates to biopolymers, temperature-sensitive and bioactive surfaces comprising same and the use thereof for cell harvesting.

The temperature-sensitive nature of the biopolymers of the invention allows rapid and efficient cell harvesting as a result of a simple temperature change, achieving a viability higher than that achieved with other procedures described in the prior art. In addition, as it is possible to design biopolymers with specific cell-binding sequences for one or more cell types, it is possible to construct selective substrates for tissue engineering.

The systems described in the prior art present some deficiencies as, for example, part of the polymer deposited in the surface is introduced into the sheets or cells harvested as a contaminant that is carried over into subsequent stages, with the risks this entails, and it is still not possible to efficiently group or arrange different cell types in a sheet in an ordered or structured manner. In this sense, the polymer of the invention presents a major advantage as, instead of being deposited on the surface in an indiscriminate manner, said polymer is grafted in a controlled manner by way of a covalent bond such that the system continues to be temperature sensitive and useful for cell harvesting.

The authors of the present invention have described a surface cell-culture system that allows cell harvesting in a simple and efficient manner. The surface on which the cells are cultured is modified to allow the covalent binding of temperature-sensitive biopolymers, which in turn selectively bind different cell types. The cells bound to the surface can be released by way of a simple temperature change, preserving the cell surface proteins and maintaining high cell viability. Moreover, cells can bind to the entire culture surface or locally.

As the temperature-sensitive biopolymers used are grafted to the surface via covalent bonds, release of the tissue generated occurs without carrying over biopolymer residues.

In general, the biopolymer of the present invention is based on repetitions of domains found in natural elastin, which are non-toxic and therefore suitable for interaction with cells. Moreover, said biopolymer presents a central bioactive domain based on a cell-binding sequence and a domain containing reactive groups, such as the amino group of lysine for example, for covalent bonding to the culture surface.

The biopolymer of the present invention has been produced using recombinant DNA technology.

Likewise, the invention relates to any of the nucleic acids that code for the amino acid sequence of the biopolymers of the invention, the uses thereof and a method for synthesising same.

Surfaces bioactivated with grafted polymers are produced in the present invention using "click" chemistry. Said surfaces, which induce selective cell adhesion, cell proliferation and tissue growth thereon, respond to temperature as a system for switching and controlling the bioactivity thereof. In this manner, once the cells have been cultured or the tissue or cell layers formed, said cells, tissue or layers are detached from the surface free from damage or contamination, thus demonstrating that the cell-harvesting system is fast, simple to handle and effective. In addition, it is possible to predefine a pattern on the surface such that the cells have greater affinity for different regions of said surface and can even structure themselves into a monolayer following the same pattern.

Consequently, the invention is based on three pillars. The first of these is the possibility of nullifying the cell-adhesion ability of the scaffold as a result of the temperature sensitivity of the biopolymer. The second is the possibility to design biopolymers with different bioactivities or specific cell-binding sequences. And the third is the ability to graft the polymers to the surface in a permanent and controlled manner such that said surface retains its previous attributes.

The biopolymers have been obtained with a high degree of efficiency, complexity, control and robustness. Said attributes arise as the hydrophobic forces of the amino acids have been taken into consideration. Thus, accurate and quantitative control of the inverse transition phenomenon that occurs in these materials, and therefore of the temperature ($T_t$) at which these polymers change from being bioactive to non-bioactive, is possible.

The biopolymers have been obtained using recombinant DNA technology by cloning a nucleic acid sequence that codes for the amino acid sequence of the biopolymer of the present invention in a vector that is able to express said sequence. This technology makes use of the replication, transcription and translation machinery of the organisms to produce the biopolymers.

The biopolymers of the invention contain elastin-like lateral domains that endow said biopolymers with the necessary temperature responsiveness. In addition, the biopolymers contain a central bioactive domain containing a cell-binding sequence (RGD, REDV, etc.). Finally, said biopolymers contain a chemically reactive domain at their termini, such as the amino groups of lysine for example (FIG. 1).

Grafting of the polymer to the surface is performed by activating said surface followed by the biofunctionalisation thereof by covalent bonding via a "click"-type cyclisation reaction. Once biofunctionalised, cells are seeded onto the surface and cultured until tissue formation has occurred. At this stage the temperature is reduced to a value lower than the transition temperature for the bioactive polymer, thereby modifying the conformation of said polymer to give a non-adherent substrate from which the cell layer separates spontaneously.

The explanation of the adhesion-separation phenomenon at a molecular level is based on a self-organisation of the molecular chains on the nanoscale, said organisation occurring as a result of temperature changes in the system. In this process, at the culture temperature and in the presence of water, said chains are present in a folded conformation in which the polar cell-binding domains tend to be exposed to the exterior. Upon decreasing the temperature, these chains unfold, leaving the cell-binding domains inaccessible to cells and forming a non-adherent surface from which the cells detach (FIG. 2).

Consequently, a first aspect of the present invention relates to a biopolymer comprising peptides A, B and D, with the structure [(D-B$_n$-A$_m$-B$_s$)], where A has the structure (F$_{t1}$-G-F$_{t2}$), where F has the structure $X_1$-$X_2$-$X_3$-$X_4$-$X_5$, where $X_1$ and $X_4$ may be any amino acid except the amino acids proline, lysine, serine and cysteine, $X_2$ is the amino acid proline, $X_3$ may be the amino acid glycine or the amino acid alanine and $X_5$ is the amino acid glycine, G is a cell-binding sequence, t1 and t2 have values of between 8 and 12, B has the structure $Y_1$-$Y_2$-$Y_3$-$Y_4$-$Y_5$, where $Y_1$ and $Y_4$ may be any amino acid except the amino acids proline, lysine, serine and cysteine, $Y_2$ is the amino acid proline, $Y_3$ may be the amino acid glycine or the amino acid alanine and $Y_5$ is the amino acid glycine, D comprises a peptide of 2 to 10 identical or different amino acids selected from a list comprising lysine, cysteine, serine, asparagine, glutamine, aspartic acid and glutamic acid, n has a value of between 10 and 18, m has a value of between 1 and 3, and s has a value of between 10 and 18.

Peptide A is the bioactive amino acid sequence comprising the cell-binding sequence. Both peptide B and peptide F are elastin-like domains. Peptide D is the reactive domain as said peptide contains the polar amino acids that will allow covalent grafting of the biopolymer to the surface via the reactive groups contained in the side chains thereof.

In accordance with the structures described that give rise to the biopolymers of the invention, the amino acid sequences (the term "peptides" can be used indistinctly to refer to the amino acid sequences) A, B, D, F and G may be bound covalently or via any other type of bond that leads to a structure which maintains the properties of the biopolymers of the present invention. Said bond may be selected from, but is not limited to, the list comprising hydrogen bonds, ion pairing, hydrophobic association or inclusion complex formation.

In a preferred embodiment of the biopolymer of the first aspect of the present invention, G is an amino acid sequence comprising a peptide selected from amongst the list comprising RGD, LDT, SEQ ID NO. 16, SEQ ID NO. 17, SEQ ID NO. 18 or SEQ ID NO. 19, or a heparin-binding domain or a binding domain for lecithin- or agglutinin-derived sugars. Preferably, G comprises the domain RGD. More preferably, G is SEQ ID NO. 1.

The RGD domain is well known and comprises, as its name indicates, the amino acids arginine, glycine and aspartic acid. Said domain is recognised by proteins from the cell surface of various cell types and functions as a cell-adhesion domain. SEQ ID NO. 16 is the REDV domain, which is also well known and comprises, as its name indicates, the amino acids arginine, glutamic acid, aspartic acid and valine; said domain also functions as a cell-adhesion domain and is recognised by endothelial cells. A heparin-binding domain functions as a cell-binding domain as said domain binds to glycosaminoglycans on the cell surface. Likewise, a sugar-binding domain allows binding to cells via the sugars presented by membrane glycoproteins. Lecithin and agglutinin have well-known sugar-binding domains. SEQ ID NO. 18 is present in laminin and is recognised by various cell types, SEQ ID NO. 19 is recognised by neurites, in other words any projection from the soma of a neuron, whether a dendrite or an axon. These sequences, which form part of the biopolymer of this invention, are recognised by their respective cell types and promote the binding thereof. Those biopolymers containing SEQ ID NO: 16 or SEQ ID NO. 19 an be used to generate vascular tissue or nerve tissue, respectively.

The G domain must present an effective cell-binding sequence in order for the biopolymer of the invention to operate adequately as a cell-harvesting system, as shown by the examples of the present invention.

In a preferred embodiment of the biopolymer of the first aspect of the present invention, $X_1$ is the amino acid valine, leucine or isoleucine. Preferably, F is SEQ ID NO. 2.

In a preferred embodiment of the biopolymer of the first aspect of the present invention, $Y_1$ is the amino acid valine, leucine or isoleucine. Preferably, B is SEQ ID NO. 3.

In a preferred embodiment of the biopolymer of the first aspect of the present invention, D comprises a peptide of 3 to 5 identical or different amino acids selected from a list comprising lysine, cysteine, serine, asparagine, glutamine, aspartic acid and glutamic acid.

In a preferred embodiment of the biopolymer of the first aspect of the present invention, the identical or different amino acids of the peptide of which D is comprised are selected from a list comprising lysine, cysteine, serine, asparagine and glutamine. Preferably, the amino acids of the peptide of which D is comprised are equal and are the amino acid lysine.

Domain D must comprise at least two amino acids the side chain of which presents a reactive group, said group being necessary for the reaction that will allow grafting of the biopolymer molecule to the culture surface via one of the ends thereof by way of covalent bonds. Consequently, D comprises between 2 and 10 polar amino acids with a reactive group in the side chain (such as lysine, cysteine, serine, asparagine, glutamine, aspartic acid and glutamic acid), preferably between 3 and 5 of such amino acids.

The amino acids lysine, cysteine, serine, asparagine and glutamine are preferred for covalent bonding between the biopolymer and the surface by modification of the amine groups in the side chains of said amino acids to azide. When such amino acids are used in the D domain, said domain is located at the N-terminal end of the biopolymer. Lysine is the preferred amino acid for forming covalent bonds between the D domain of the biopolymer and the culture surface due to the ease with which the amino group in the side chain thereof undergoes a nucleophilic substitution reaction with the azide reagent, as can be seen in the examples of the present invention.

Amino acids with a carboxyl group in the side chain, such as aspartic acid and glutamic acid, may also be used to covalently bind the end of the biopolymer to the surface, although in this case by way of other reactions well known to a person skilled in the art. When such amino acids are used in the D domain, said domain is located at the C-terminal end of the biopolymer as the terminal carboxyl group of the biopolymer itself may also participate in covalent bond formation with the surface.

Lysine is the preferred amino acid for forming covalent bonds between the D domain of the biopolymer and the culture surface due to the ease with which the amino group in the side chain thereof undergoes a nucleophilic substitution reaction with the azide reagent, as can be seen in the examples of the present invention.

In a preferred embodiment of the biopolymer of the first aspect of the present invention, t1 and t2 have values of between 9 and 11.

In a preferred embodiment of the biopolymer of the first aspect of the present invention, n has a value of between 12 and 16.

In a preferred embodiment of the biopolymer of the first aspect of the present invention, m has a value of between 1 and 2.

In a preferred embodiment of the biopolymer of the first aspect of the present invention, s has a value of between 12 and 16.

In a preferred embodiment of the biopolymer of the first aspect of the present invention, D is the peptide SEQ ID No. 4, B is the peptide SEQ ID No. 3, n and s have a value of 14, F is the peptide SEQ ID No. 2, t1 and t2 have a value of 10, G is the peptide SEQ ID No. 1 and m has a value of 2.

A second aspect of the present invention relates to a nucleic acid comprising a nucleotide sequence that codes for the amino acid sequence of the biopolymer of the first aspect of the invention. Said nucleic acid is preferably an expression vector.

The term "expression vector" (hereinafter vector of the invention or vector of the present invention) relates to a DNA fragment that is able to replicate itself in a certain host and, as the term suggests, may serve as a vehicle for multiplying another DNA fragment (insert) fused to it. Insert relates to a DNA fragment that is fused to the vector; in the case of the present invention, the vector may comprise any of the nucleotide sequences that code for any of the biopolymers of the invention, fused to it, that may replicate itself in an appropriate host. The vectors may be plasmids, cosmids, bacteriophages or viral vectors, without excluding any other type of vector that corresponds to the given definition of a vector.

A third aspect of the present invention relates to an isolated cell transfected with the nucleic acid of the second aspect of the invention.

The term cell, as used in the present invention, refers to a prokaryotic or eukaryotic cell. The cell may be a bacterium capable of replicating a transformed external DNA, such as any of the strains of the species *Escherichia coli*, or a bacterium capable of transferring the DNA of interest to the interior of a plant, such as *Agrobacterium tumefaciens*. Preferably the cell refers to a eukaryotic plant cell, and within this group, more preferably, to those cells belonging to the kingdom *Plantae*. Thus, in the case where the cell is a plant cell, the term cell comprises at least a parenchymal cell, a meristematic cell or any type of differentiated or undifferentiated cell. Likewise, a protoplast (a plant cell lacking a cell wall) is also covered by this definition.

The term "transfection" refers to the introduction of external genetic material into cell using plasmids, viral vectors (the term transduction is also used in this case) or other transfer tools. For non-viral methods, the term transfection is used to refer to eukaryotic mammalian cells, whereas the term transformation is preferred to describe the non-viral transfer of genetic material in bacteria and non-animal eukaryotic cells such as fungi, alga or plants.

A fourth aspect of the present invention relates to use of the biopolymer of the first aspect of the invention, the nucleic acid of the second aspect of the invention, or the cell of the third aspect of the invention to prepare a cell-harvesting scaffold.

The term cell-harvesting "scaffold" is a surface of any type to which cells can adhere. A large number of cell-culture scaffolds, such as plates, particles, flasks, cuvettes, porous surfaces membranes, and so on, which may comprise one or more materials, such as plastics prepared for cell culture, glass, and others, which in turn may be pretreated with one or more molecules that allow and promote said cell culture, such as fibronectin, collagen, laminin, polylysine, polyornithine, etc. are known. The scaffold relates only to the surface on which cells are seeded and does not include other accessories such as stoppers, covers, etc.

A fifth aspect of the present invention relates to a cell-harvesting scaffold comprising the biopolymer of the first aspect of the invention. The connection between the biopolymer and the scaffold preferably involves at least two covalent bonds per biopolymer molecule, more preferably three covalent bonds per biopolymer molecule. Preferably, the amino groups or carboxyl groups of the side chains of at least two of the amino acids from peptide D react to form the covalent bonds. The surface of the scaffold is preferably smooth or curved. More preferably, the scaffold comprises microparticles. Preferably, said microparticles are spherical or pseudo-spherical.

In the case of bioreactors, it may be of greater interest to perform cell culture on microparticles than on a smooth surface or on a larger surface.

A sixth aspect of the present invention relates to use of the scaffold of the fifth aspect of the invention for cell harvesting.

A seventh aspect of the present invention relates to a cell-culture and -harvesting device comprising the scaffold of the fifth aspect of the invention.

The term cell-harvesting "device" relates to the equipment required for said cell culture, and may be a plate, including the scaffold and lid, or a culture chamber in which the scaffold comprising the biopolymer of the invention is located and which allows the conditions of temperature and $CO_2$ and $O_2$ pressure, for example, to be regulated.

An eighth aspect of the present invention relates to use of the cell-harvesting device of the seventh aspect of the invention for cell culture and harvesting. Preferably, a bioreactor is used for cell culture.

A ninth aspect of the present invention relates to a cell-harvesting method comprising the following stages:
  (a) functionalisation of a cell culture scaffold,
  (b) covalently binding the scaffold functionalised in stage (a) to at least two of the amino acids from peptide D of the biopolymer of the first aspect of the invention,
  (c) bringing a cell suspension into contact with the scaffold obtained in (b), and
  (d) harvesting the cells adhered to said scaffold.

The term "functionalise" relates to the addition of functional groups.

In a preferred embodiment of the method of the ninth aspect of the present invention, the scaffold is functionalised with alkynyl groups, alkene groups, nitrile groups, carbonyl groups or imine groups. Scaffold functionalisation is preferably performed with alkynyl groups.

In a preferred embodiment of the method of the ninth aspect of the present invention, the cells adhered to the scaffold are harvested by decreasing the temperature of the cell culture from 10 to 37° C.

In a preferred embodiment of the method of the ninth aspect of the present invention, the following stage is performed between stages (c) and (d):
  (c') culturing the cells from (c) until they proliferate and form a monolayer.

The cells in culture may divide such that, when seeded, said cells do not cover the entire culture surface and, as they divide, form a layer with a thickness of a single cell that covers the entire culture surface. This is known as forming a monolayer and achieving confluence.

In a preferred embodiment of the method of the ninth aspect of the present invention, prior to stage (b), the reactive groups in the side chains of at least two of the amino acids from peptide D of the biopolymer of the first aspect of the invention are transformed into azide groups.

In a preferred embodiment of the method of the ninth aspect of the present invention, the covalent bonding in stage (b) is performed by cycloaddition.

The cycloaddition by which the biopolymer of the invention is attached to the cell-harvesting scaffold is based on a synthetic strategy known as "click chemistry". Said strategy is based on reactions that allowing the coupling of modular blocks in an efficient and selective manner in both small-scale applications and large-scale processes. The reactions that can be considered to form part of this "click" strategy must comply with a series of well-defined requirements, such as the following: they must be modular, applicable in a wide range of situations, provide high yields, generate non-toxic substances as by-products and must be stereospecific (although not necessarily enantioselective). Moreover, such reactions must be able to be performed under mild conditions, using readily available starting products and in the absence of organic solvents, or in the presence of small quantities thereof, and the end products must be easy to isolate.

Although various types of transformations can be considered to fall within the category of "click chemistry", the Hüisgen Cu(I)-catalysed 1,3-dipolar cycloaddition of alkynes and azides, which leads to 1,2,3-triazoles, is the most well characterised and widely used example. This is due to the ease with which alkyne and azide derivatives can be synthesised, together with the kinetic stability and tolerance thereof to a wide range of functional groups and reaction conditions. Said reaction can be performed in the the presence of functional groups in essentially quantitative yields.

A tenth aspect of the present invention relates to a method for obtaining the biopolymer of the first aspect of the invention comprising the following stages:
  (a) culturing the cell of the third aspect of the invention under conditions appropriate for expression of the nucleic acid of the second aspect of the invention,
  (b) purifying the biopolymer coded by said nucleic acid.

The degree of compositional complexity imposed by the need for a multifunctional design cannot be achieved using standard macromolecular synthesis techniques. The biopolymer is obtained as a recombinant protein in genetically modified microorganisms or plants using modified molecular biological and biotechnological techniques.

The nucleotide sequence that codes for the amino acid sequence of the biopolymer of the present invention is inserted into a previously defined expression vector.

Cell transfection, as defined in a previous paragraph, is undertaken using techniques known in the prior art, for example, but not limited to, electroporation, biolistics, *Agrobacterium tumefaciens* or any other technique that allows the incorporation of any of the nucleic acids of the invention into the DNA of the host cell, whether it be genomic, chloroplastic or mitochondrial.

Expression of the nucleic acid in the cell of the invention leads to a biopolymer that can be purified using known techniques in the state of the art.

The word "comprises", and its variants, as used throughout the description and claims, is not intended to exclude other technical characteristics, additives, components or steps. For experts in the matter, other objects, advantages and characteristics of the invention will partially follow from the description and partially from the practice of the invention. The following and examples are provided by way of illustration and are not intended to limit the present invention.

DESCRIPTION OF THE DRAWINGS

FIG. 1. Scheme showing the biopolymer of the invention anchored to the culture surface. The black dots represent the reactive domains for covalent bonding to the substrate and the star shapes in the middle of the biopolymer molecule represent the cell-recognition domain.

FIG. 2. Scheme showing cell culture on the biopolymer and how cells separate when the temperature decreases from 37° C. to 4° C. as the cell-recognition domain is no longer accessible.

FIG. 3. Acrylamide gel electrophoresis of biopolymer 1, with the molecular weight marker in the left-hand lane and biopolymer 1 in the right-hand lane. Molecular weights are indicated in kilodaltons (kDa).

EXAMPLES

The invention is illustrated below by way of trials undertaken by the inventors that describe the synthesis of the biopolymer of the present invention and the features thereof. Said examples are provided in order to be able to understand the description and are not intended to limit the present invention.

Example 1

Production of Recombinant Elastin-Like Protein-Based Polymers

The synthetic nucleotide sequences that code for the amino acid sequences of the various biopolymers used, including the biopolymer of the invention, were designed and synthesised as described in WO/2010/092224. Similarly, the biopolymers were expressed, purified and characterised as described in WO/2010/092224.

The following biopolymers or polymers were designed:

```
Biopolymer 1 (371 amino acids)
Structure: D-B14-A2-B14.
Amino acid sequence SEQ ID No. 7:
MGKKKP-(VPGVG)14-((VPGIG)10AVTGRGDSPASS (VPGIG)10)2-(VPGVG)14-V
```

Coded by nucleotide sequence SEQ ID No. 8.

The theoretical amino acid composition and that obtained by high-performance liquid chromatography (HPLC) with ultraviolet (UV) detection can be found in table 1.

TABLE 1

Analysis of the amino acid composition of biopolymer 1.

|  |  | Asp | Ser | Gly | Arg | Thr | Ala |
|---|---|---|---|---|---|---|---|
| Amino acid analysis | Theoretical | 2 | 6 | 141 | 2 | 2 | 4 |
|  | Experimental | 2.63 | 5.2 | 143.6 | 2.35 | 2.06 | 4.45 |

|  |  | Pro | Val | Met | Lys | Ile | Leu |
|---|---|---|---|---|---|---|---|
| Amino acid analysis | Theoretical | 71 | 99 | 1 | 3 | 40 | 2 |
|  | Experimental | 71.48 | 96.6 | n.d. | 2.94 | 39.32 | 0.57 | n.d.: not detected.

The production yield was 75 mg/L.

Figure 4:
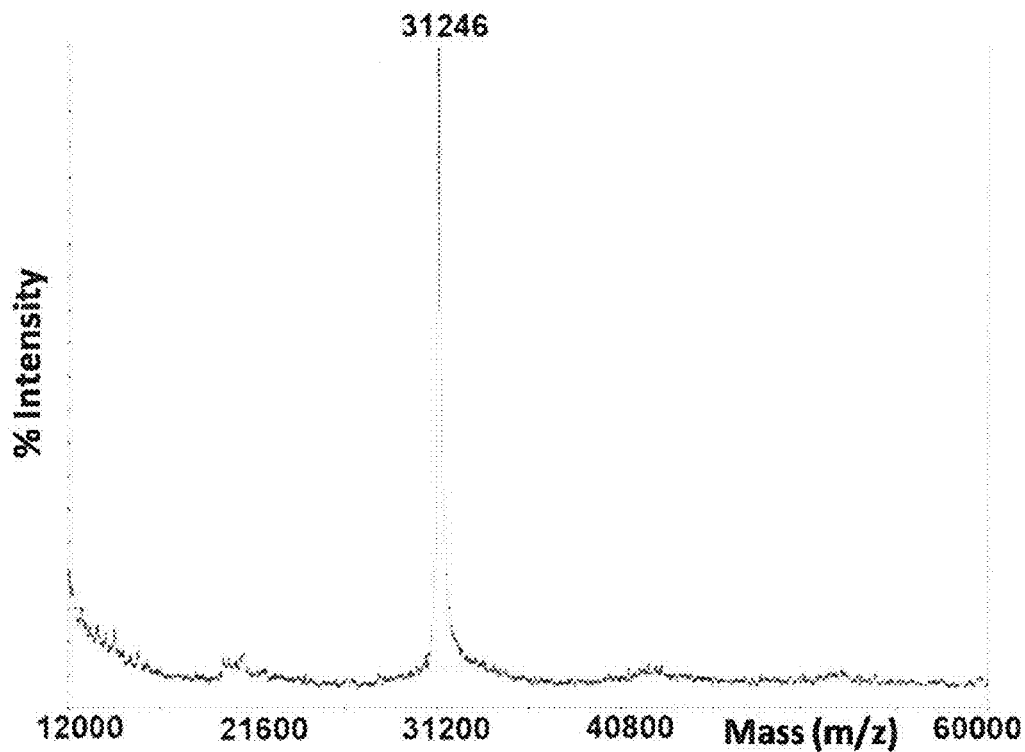
FIG. 4. Mass spectrometric (MALDI-ToF, "Matrix-assisted laser desorption/ionization—time of flight") analysis of biopolymer 1 showing an experimental molecular mass of 31,246 Da. The theoretical value is 31,371 Da and the difference between the two can be attributed to measurement error. The monodisperse character of the molecule can also be seen from the narrowness of the single peak.
Figure 5:
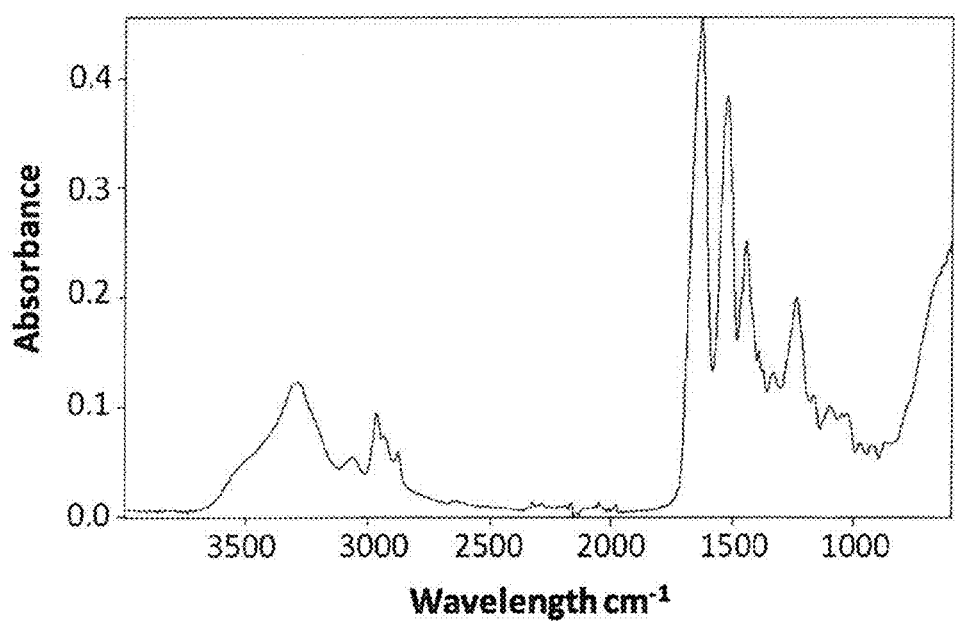
FIG. 5. Infra-red (FTIR-ATR, "Fourier Transform Infrared—Attenuated Total Reflectance") analysis of biopolymer 1 in which signals characteristic of the amide groups (~1700 $cm^{-1}$) present in the protein-based polymers designed can be seen.
Figure 6:
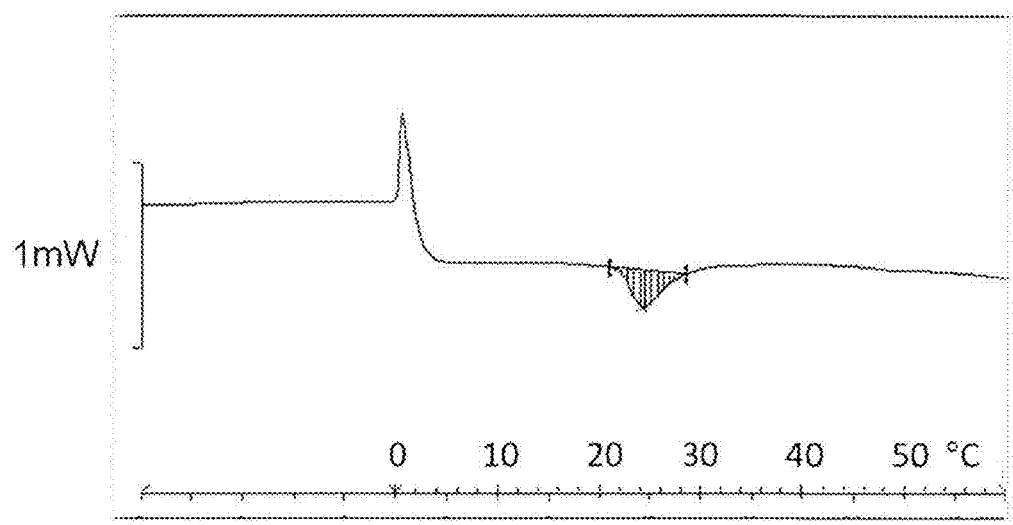
FIG. 6. Differential scanning calorimetry (DSC) analysis of biopolymer 1 in which the inverse transition temperature thereof (24.2° C.) can be seen.

The theoretical molecular weight for polymer 1 is 31,371 Da, and the value determined experimentally by polyacrylamide gel electrophoresis (FIG. 3) and MALDI-TOF using a Q-Star spectrometer was 31,250 Da (FIG. 4). FIG. 5 shows an infra-red (IR) spectrum obtained for biopolymer 1 as an example. The transition temperature obtained by DSC in phosphate-buffered saline (PBS) was 24.2° C. (FIG. 6).

Biopolymer 1 is an elastin-like polymer containing a cell-adhesion sequence that is able to operate as a cell-harvesting system. In light of the smart nature thereof, when the inverse transition temperature is exceeded the conformation thereof changes markedly, thereby nullifying the cell adhesion capabilities thereof and resulting in detachment of the cells from the surface once an effective culture of said cells has been achieved.

Amino acid sequence A includes a non-specific bioactive RGD sequence, which induces cell adhesion to the bioactive surface at temperatures above the inverse transition temperature coincident with the cell culture temperature.

Amino acid sequence B is included as a carrier of the smart properties of the polymer, producing a different conformation of the polymer depending on the temperature of the environment, and said sequence prevents cell adhesion below the inverse transition temperature by nullifying the effect of cell-adhesion sequence A.

Amino acid sequence D includes three lysine amino acids that bear the amino groups required for binding the polymer to the surface via a covalent chemical bond, in other words for obtaining the biofunctionalised surfaces.

```
Biopolymer 2 (371 amino acids)
Structure: D-B₁₄-C₂-B₁₄
Amino acid sequence SEQ ID No. 9:
MGKKKP-(VPGVG)₁₄-((VPGIG)₁₀AVTGRDGSPASS (VPGIG)₁₀)₂-(VPGVG)₁₄-V
```

Coded by nucleotide sequence SEQ ID No. 10.

The theoretical amino acid composition and that obtained by HPLC with UV detection can be found in table 2.

TABLE 2

Analysis of the amino acid composition of biopolymer 2.

|  |  | Asp | Ser | Gly | Arg | Thr | Ala |
|---|---|---|---|---|---|---|---|
| Amino acid analysis | Theoretical | 2 | 6 | 141 | 2 | 2 | 4 |
|  | Experimental | 2.00 | 5.98 | 141.40 | 2.00 | 2.00 | 4.30 |

TABLE 2-continued

Analysis of the amino acid composition of biopolymer 2.

|  |  | Pro | Val | Met | Lys | Ile | Leu |
|---|---|---|---|---|---|---|---|
| Amino acid analysis | Theoretical | 71 | 99 | 1 | 3 | 40 | 2 |
|  | Experimental | 71.00 | 98.70 | 1.00 | 2.97 | 39.40 | 2.00 |

The production yield was 70 mg/L.

The theoretical molecular weight for polymer 2 is 31,371 Da, and the value determined experimentally by polyacrylamide gel electrophoresis and MALDI-TOF using a Q-Star spectrometer was 31,265 Da. The transition temperature obtained by DSC in PBS was 23.5° C.

Polymer 2 may be able to act as a cell-harvesting system. In light of the smart nature thereof, when the inverse transition temperature is exceeded the conformation thereof changes markedly and cell adhesion decreases, thereby resulting in detachment of the cells from the surface once an effective culture of said cells has been achieved.

Like polymer 1, polymer 2 possess the amino acid sequences B and D. Amino acid sequence C includes a non-bioactive polar RDG sequence.

```
Biopolymer 3 (427 amino acids)
Structure: D-B₈₄
Amino acid sequence SEQ ID No. 11:
MGKKKP-(VPGVG)₈₄-V
```

Coded by nucleotide sequence SEQ ID No. 12.

The theoretical amino acid composition and that obtained by HPLC with UV detection can be found in table 3.

TABLE 3

Analysis of the amino acid composition of biopolymer 3.

|  |  | Gly | Pro | Val | Met | Lys |
|---|---|---|---|---|---|---|
| Amino acid analysis | Theoretical | 169 | 85 | 169 | 1 | 3 |
|  | Experimental | 172.00 | 85.40 | 166.00 | n.d. | 2.99 |

The production yield was 35 mg/L.

The theoretical molecular weight for polymer 3 is 35,191 Da, and the value determined experimentally by polyacrylamide gel electrophoresis and MALDI-TOF using a Q-Star spectrometer was 35,152 Da. The transition temperature obtained by DSC in PBS was 29.4° C.

The elastin-like polymer known as polymer 3 is able to act as a cell-harvesting system due to the smart nature thereof, although the number of cells adhered is lower due to the lack of a bioactive cell-adhesion sequence. Amino acid sequences B and D are the same as those in polymers 1 and 2.

```
Biopolymer 4 (371 amino acids)
Structure: B₁₄-A₂-B₁₄
Amino acid sequence SEQ ID No. 13:
MESLLP-(VPGVG)₁₄-((VPGIG)₁₀AVTGRDGSPASS (VPGIG)₁₀)₂-(VPGVG)₁₄-V
```

Coded by nucleotide sequence SEQ ID No. 14.

The theoretical amino acid composition and that obtained by HPLC with UV detection can be found in table 4.

TABLE 4

| Analysis of the amino acid composition of biopolymer 4. | | | | | | | |
|---|---|---|---|---|---|---|---|
| | | Asp | Ser | Glu | Gly | Arg | Thr |
| Amino acid analysis | Theoretical | 2 | 7 | 1 | 140 | 2 | 2 |
| | Experimental | 2.11 | 6.44 | 1.14 | 144.29 | 2.75 | 1.95 |
| | | Ala | Pro | Val | Met | Lys | Ile | Leu |
| Amino acid analysis | Theoretical | 4 | 71 | 99 | 1 | 0 | 40 | 2 |
| | Experimental | 4.09 | 70.62 | 95.89 | n.d. | 0.00 | 39.20 | 2.27 |

The production yield was 42 mg/L.

The theoretical molecular weight for polymer 4 is 31,371 Da, and the value determined experimentally by polyacrylamide gel electrophoresis and MALDI-TOF using a Q-Star spectrometer was 31,388 Da. The transition temperature obtained by DSC in PBS was 23.8° C.

Polymer 4 is used in a system comprising two biopolymers, the first of which, polymer 3, is able to graft to the surface and the second of which, polymer 4, is able to induce cell adhesion such that the system is useful as a cell-harvesting system due to the synergy between the effects of each polymer.

In another experiment performed, polymer 4 is used grafted to the surface once the terminal amino group thereof has been modified to an azide group and without containing the lysine-rich sequence D at the amino-terminus.

Amino acid sequences A and B are the same as those in polymer 1.

```
Biopolymer 5 (699 amino acids)
Structure: H-I₆
Amino acid sequence SEQ ID No. 15:
MGSSHHHHHHSSGLVPRGSH-MESLLP-{[(VPGIG)₂

(VPGKG) (VPGIG)₂]₂AVTGRGDSPASS

[(VPGIG)₂(VPGKG) (VPGIG)₂]₂]}₆-V
```

Coded by the nucleotide SEQ ID No. 20.

The theoretical amino acid composition and that obtained by HPLC with UV detection can be found in table 5.

TABLE 5

| Analysis of the amino acid composition of biopolymer 5. | | | | | | | |
|---|---|---|---|---|---|---|---|
| | | Asp | Ser | Glu | Gly | Arg | Thr |
| Amino acid analysis | Theoretical | 6 | 24 | 1 | 255 | 7 | 6 |
| | Experimental | 5.22 | 21.67 | 1.15 | 253.12 | 6.95 | 5.65 |
| | | Ala | Pro | Val | Met | Lys | Ile | Leu |
| Amino acid analysis | Theoretical | 12 | 128 | 128 | 2 | 24 | 96 | 3 |
| | Experimental | 11.85 | 130.23 | 127.95 | n.d. | 23.55 | 96.87 | 3.95 |

The production yield was 51 mg/L.

The theoretical molecular weight for polymer 5 is 60,661 Da, and the value determined experimentally by polyacrylamide gel electrophoresis and MALDI-TOF using a Q-Star spectrometer was 60,556 Da. The transition temperature obtained by DSC in PBS was 32.2° C.

Amino acid sequence I is similar to sequence A, which carries the cell-adhesion sequence RGD, but with the peculiarity that one isoleucine amino acid from the pentapeptide in position 3 and from the pentapeptide in position 8 of the series of 10 pentapeptides that flank the RGD adhesion sequence has been replaced by a lysine, which carries amino groups that can be transformed into azide groups. In this manner, said sequence binds to the surface via multiple covalent bonds spread throughout the chain of biopolymer 5, thus preventing the conformation of said chain from varying markedly with temperature and therefore proving to be a less effective cell-harvesting system

```
Biopolymer 6 (343 amino acids)
Structure: D-A₃
Amino acid sequence SEQ ID No. 21:
MGKKKP-((VPGIG)₁₀AVTGRGDSPASS (VPGIG)₁₀)₃-V
```

Coded by nucleotide sequence SEQ ID No. 22.

The theoretical amino acid composition and that obtained by HPLC with UV detection can be found in table 6.

TABLE 6

Analysis of the amino acid composition of biopolymer 6.

|  |  | Asp | Ser | Gly | Arg | Thr | Ala |
|---|---|---|---|---|---|---|---|
| Amino acid analysis | Theoretical | 3 | 9 | 127 | 3 | 3 | 6 |
| | Experimental | 3.14 | 8.57 | 128.25 | 3.19 | 2.87 | 6.05 |

|  |  | Pro | Val | Met | Lys | Ile |
|---|---|---|---|---|---|---|
| Amino acid analysis | Theoretical | 64 | 64 | 1 | 3 | 60 |
| | Experimental | 64.57 | 65.11 | n.d. | 2.85 | 61.62 |

The production yield was 83 mg/L.

The theoretical molecular weight for polymer 6 is 29461 Da, and the value determined experimentally by polyacrylamide gel electrophoresis and MALDI-TOF using a Q-Star spectrometer was 29,269 Da. The transition temperature obtained by DSC in PBS was 23.0° C.

The elastin-like polymer known as polymer 6 contains amino acid sequence A, which carries the RGD cell-adhesion sequence repeated three times along the polypeptide chain and contains sequence D, which is the same as in polymers 1-3, thus allowing said polymer to be covalently bound to the scaffold.

Example 2

Modification of Polymers 1-6

Modification of Biopolymer 1 to Obtain Biopolymer 1'

Biopolymer 1' is obtained by transformation of the sequence for peptide D, which contains lysine amino acids bearing amino groups in the gamma position. Said amino groups are transformed in order to subsequently perform a "click"-type cyclisation. The transformed peptide D is termed peptide E.

Figure 7:
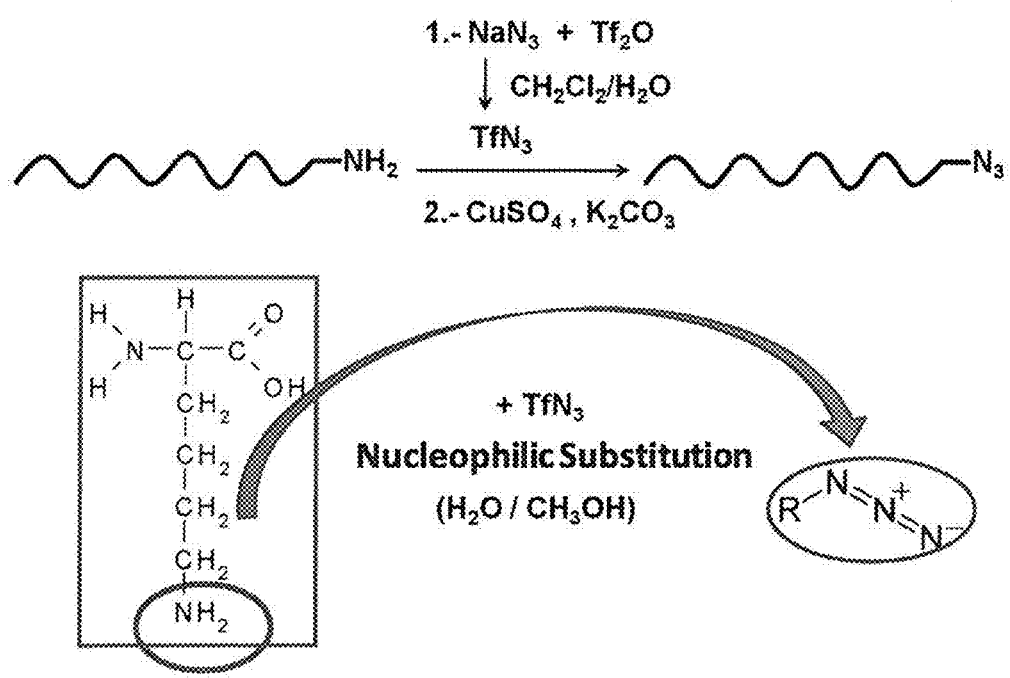
FIG. 7. Functionalisation of the polymers with azide groups. Initially (1), triflic azide $TfN_3$ is generated "in situ" from the corresponding, less reactive sodium azide. In a second step (2), triflic azide acts as a nucleophile in a substitution reaction with the amino group.

The amino groups of the lysines in peptide E have been transformed into azide groups by way of a substitution reaction using triflic azide generated "in situ" as nucleophile (FIG. 7), obtaining a reaction yield of 89%. This leads to a smart polymer containing a bioactive cell-adhesion sequence which can be chemically grafted to the surface.

Figure 8:
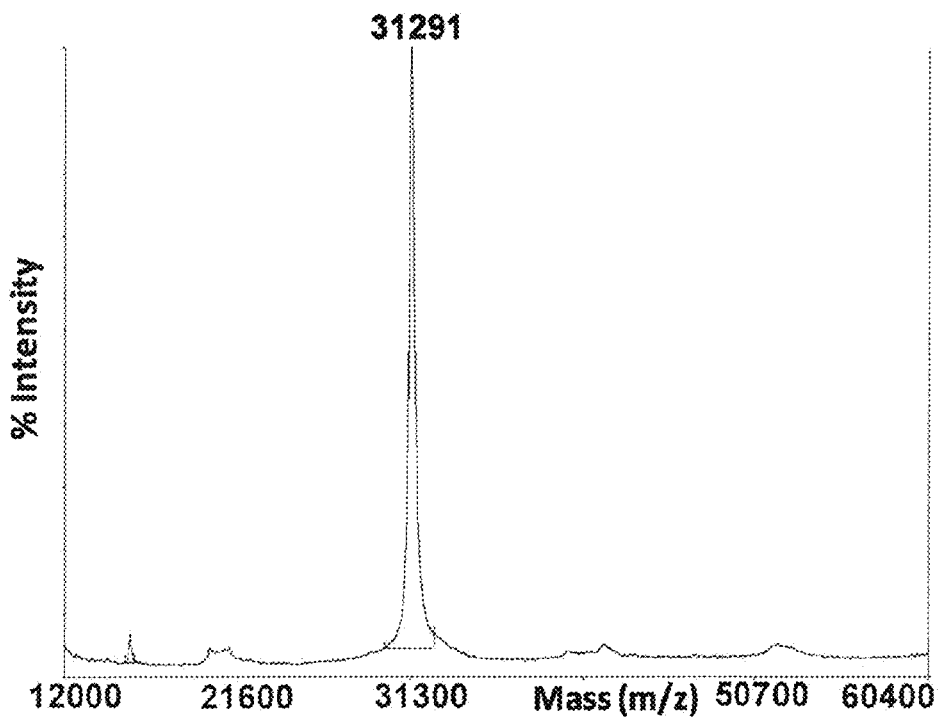
FIG. 8. Mass spectrometric (MALDI-ToF) analysis of biopolymer 1' showing the molecular weight increase of 46 units with respect to the weight of precursor biopolymer 1 due to the introduction of azide groups, which have a mass 24 units higher than that of amino groups.

Biopolymer 1' was characterised by MALDI-TOF spectrometry, said analysis giving a molecular weight of 31,296 Da for the polymer (theoretical molecular weight of 31,475 Da, FIG. 8), with a logical increase of 46 g/mol being observed due to transformation of the amino groups of the lysines contained therein into azide groups.

Figure 9:
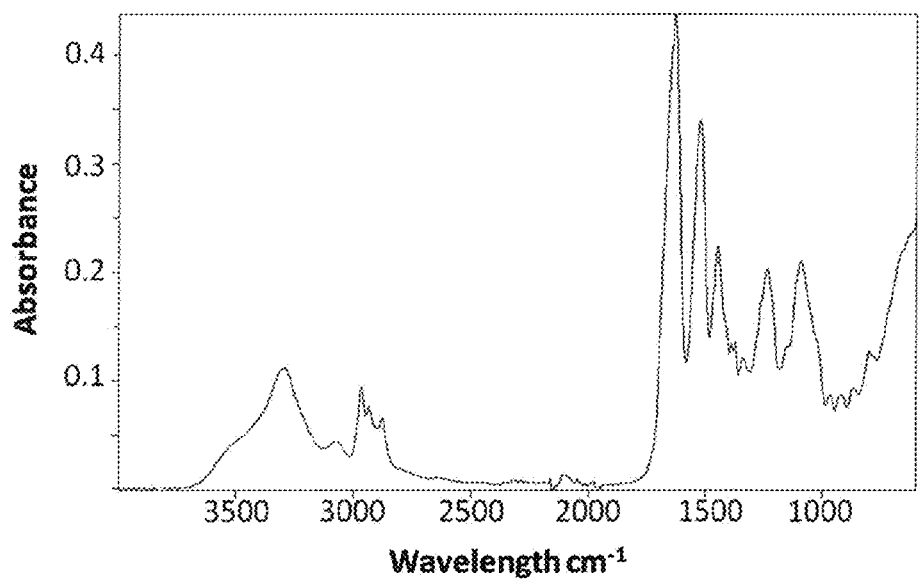
FIG. 9. Infra-red (FTIR-ATR) spectroscopic analysis of biopolymer 1' showing the presence of absorption bands characteristic of amide groups from the protein-based polymers (~1700 $cm^{-1}$) together with a characteristic signal for the new azide group at 2100 $cm^{-1}$.
Figure 10:
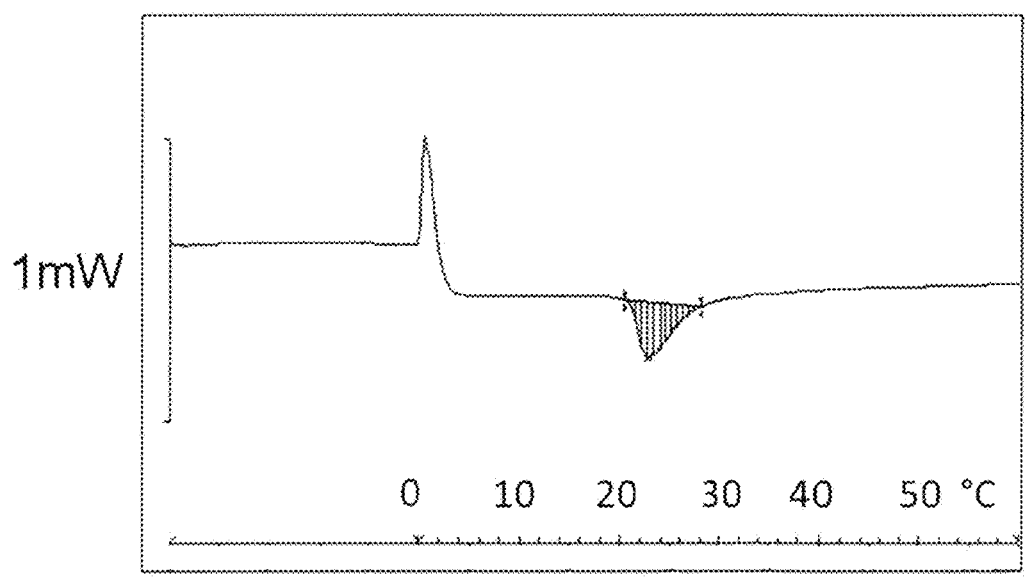
FIG. 10. DSC analysis of biopolymer 1' showing the 1.3° C. decrease in the inverse transition temperature of said biopolymer (22.8° C.) with respect to its precursor (24.2° C.) due to the introduction of less polar groups such as azides into the structure thereof.

The infra-red (FTIR-ATR) spectrum of the biopolymer 1' obtained presents a signal characteristic of azide groups at a frequency of 2100 cm$^{-1}$ (FIG. 9), whereas no such signal is observed in the IR spectrum of the precursor biopolymer 1 (FIG. 5).

The success and scope of the modification reaction for polymer 1 was confirmed by examining the amino acid analysis performed for biopolymer 1', which showed a marked decrease in the number of lysine amino acids, with the other amino acids remaining unaltered. In this manner, we can deduce that the amino groups of said lysines have been modified and transformed into azide groups, with 46% of said lysines estimated to have been transformed (table 7).

TABLE 7

Analysis of the amino acid composition of biopolymer 1'.

|  |  | Asp | Ser | Gly | Arg | Thr | Ala |
|---|---|---|---|---|---|---|---|
| Amino acid analysis | Theoretical | 2 | 6 | 141 | 2 | 2 | 4 |
| | Experimental | 1.73 | 5.5 | 143.05 | 2.28 | 2.16 | 4.33 |

|  |  | Pro | Val | Met | Lys | Ile | Leu |
|---|---|---|---|---|---|---|---|
| Amino acid analysis | Theoretical | 71 | 99 | 1 | 3 | 40 | 2 |
| | Experimental | 71.22 | 96.05 | n.d. | 1.61 | 40.23 | 0.51 |

The smart response of biopolymer 1' occurs at a temperature of 22.8° C., 1.3° C. lower than the value for biopolymer 1 (24.2° C.). This behaviour is due to the introduction of a strongly apolar group, namely the azide group, with respect to the starting amino group (FIG. 6).

Modification of Biopolymers 2-6 to Obtain Biopolymers 2'-6'

Biopolymers 2-6 were modified as described for biopolymer 1 to give biopolymers 2'-6', respectively.

The modified polymers were characterised in a similar manner to 1'. An amino acid analysis of said polymers was performed, the molecular weights (by MALDI-TOF) and inverse transition temperatures (by DSC) thereof were determined, and the infra-red (FTIR-ATR) spectra thereof analysed, all of which led to similar conclusions to those reached previously. All these data are detailed below.

Modified Biopolymer 2'

TABLE 8

Analysis of the amino acid composition of biopolymer 2'.

|  |  | Asp | Ser | Gly | Arg | Thr | Ala |
|---|---|---|---|---|---|---|---|
| Amino acid analysis | Theoretical | 2 | 6 | 141 | 2 | 2 | 4 |
| | Experimental | 2 | 6.36 | 144.53 | 2.35 | 2.19 | 4.8 |

|  |  | Pro | Val | Met | Lys | Ile | Leu |
|---|---|---|---|---|---|---|---|
| Amino acid analysis | Theoretical | 71 | 99 | 1 | 3 | 40 | 2 |
| | Experimental | 70.76 | 94.87 | n.d. | 1.62 | 40.3 | 0.38 |

Reaction yield: 94%
Theoretical molecular weight: 31,475 Da
Mean experimental molecular weight (MALDI-TOF): 31,291 Da
Transition temperature (DSC) in PBS: 21.8° C.
Lysine transformation rate: 46%
Modified Biopolymer 3'

TABLE 9

Analysis of the amino acid composition of biopolymer 3'.

|  |  | Gly | Pro | Val | Met | Lys |
|---|---|---|---|---|---|---|
| Amino acid analysis | Theoretical | 169 | 85 | 169 | 1 | 3 |
| | Experimental | 169.39 | 97.84 | 154.78 | n.d. | 1.51 |

Reaction yield: 80%
Theoretical molecular weight: 35,295 Da
Mean experimental molecular weight (MALDI-TOF): 35,185 Da
Transition temperature (DSC) in PBS: 27.7° C.
Lysine transformation rate: 50%
Modified Biopolymer 4'

TABLE 10

Analysis of the amino acid composition of biopolymer 4'.

|  |  | Asp | Ser | Glu | Gly | Arg | Thr |
|---|---|---|---|---|---|---|---|
| Amino acid analysis | Theoretical | 2 | 7 | 1 | 140 | 2 | 2 |
| | Experimental | 2.35 | 6.83 | 1.25 | 145.53 | 2.64 | 2.11 |

|  |  | Ala | Pro | Val | Met | Lys | Ile | Leu |
|---|---|---|---|---|---|---|---|---|
| Amino acid analysis | Theoretical | 4 | 71 | 99 | 1 | 0 | 40 | 2 |
| | Experimental | 4.22 | 70.15 | 97.78 | n.d. | 0.00 | 39.40 | 2.14 |

Reaction yield: 90%
Theoretical molecular weight: 31398 Da
Mean experimental molecular weight (MALDI-TOF): 31,327 Da
Transition temperature (DSC) in PBS: 24.2° C.
Modified biopolymer 5'

TABLE 11

Analysis of the amino acid composition of biopolymer 5'.

|  |  | Asp | Ser | Glu | Gly | Arg | Thr | Ala |
|---|---|---|---|---|---|---|---|---|
| Amino acid analysis | Theoretical | 6 | 24 | 1 | 255 | 7 | 6 | 12 |
| | Experimental | 4.83 | 20.33 | 1.04 | 252.67 | 7.31 | 5.71 | 11.94 |

|  |  | Pro | Val | Met | Lys | Ile | Leu |
|---|---|---|---|---|---|---|---|
| Amino acid analysis | Theoretical | 128 | 128 | 2 | 24 | 96 | 3 |
| | Experimental | 131.42 | 128.55 | n.d. | 8.49 | 97.74 | 4.62 |

Reaction yield: 85%
Theoretical molecular weight: 61,285 Da
Mean experimental molecular weight (MALDI-TOF): 60,900 Da
Transition temperature (DSC) in PBS: 22.2° C.
Lysine transformation rate: 54%
Modified biopolymer 6'

TABLE 12

Analysis of the amino acid composition of biopolymer 6'.

|  |  | Asp | Ser | Gly | Arg | Thr | Ala |
|---|---|---|---|---|---|---|---|
| Amino acid analysis | Theoretical | 3 | 9 | 127 | 3 | 3 | 6 |
| | Experimental | 3.08 | 8.92 | 129.16 | 3.26 | 2.74 | 6.18 |

|  |  | Pro | Val | Met | Lys | Ile |
|---|---|---|---|---|---|---|
| Amino acid analysis | Theoretical | 64 | 64 | 1 | 3 | 60 |
| | Experimental | 65.15 | 64.58 | n.d. | 0.52 | 60.83 |

Reaction yield: 50%
Theoretical molecular weight: 29,565 Da
Mean experimental molecular weight (MALDI-TOF): 29,302 Da
Transition temperature (DSC) in PBS: 21.5° C. Lysine transformation rate: 83%

Example 3

Production of Polymer-Biofunctionalised Surfaces

Once the biopolymers had been modified with azide groups, biofunctionalised surfaces were obtained in two steps: the first step comprised activation of the glass surface with alkynyl groups and the second step grafting of the polymers to said surface via a covalent chemical bond.

Surface Activation

Figure 11:
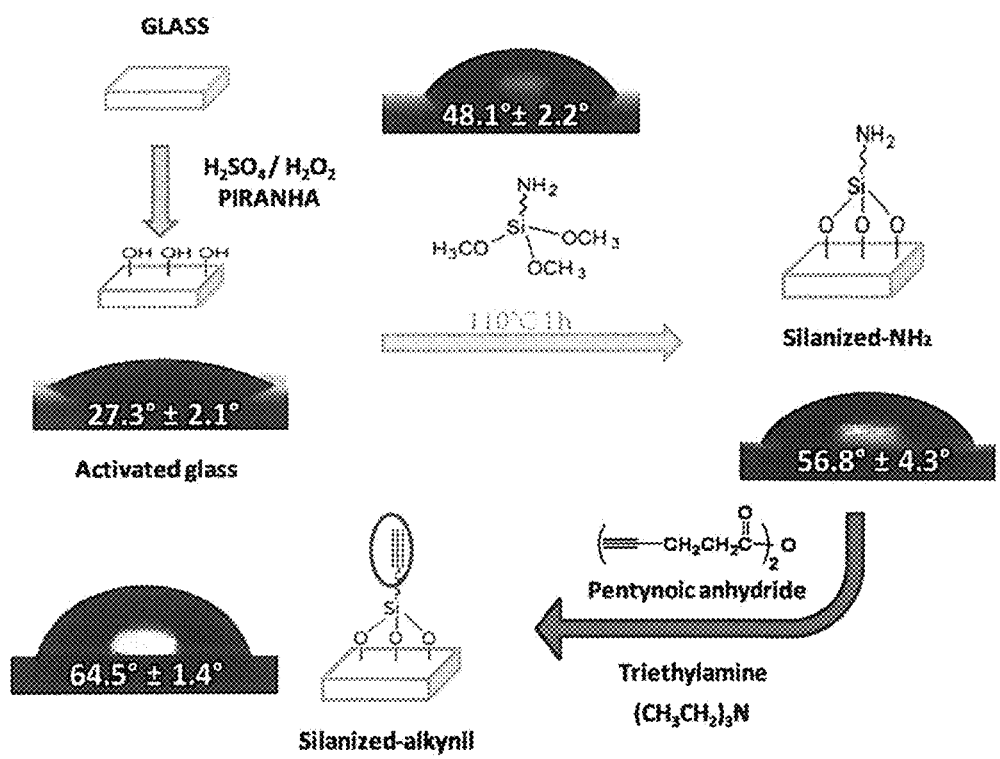
FIG. 11. Scheme showing the surface functionalisation steps. In the first step the surface is activated with hydroxyl groups using a reagent such as piranha solution. In the following step the amino group-functionalised surface is generated by covalent bonding between the silanol generated "in situ" and the hydroxyl groups. In the third step the amino groups are modified by amidation to give the surface activated with the alkynyl groups present at the end of the reagent molecule used.

First of all the surface was activated with "piranha" solution, a 7:3 mixture by volume of sulfuric acid ($H_2SO_4$) and hydrogen peroxide ($H_2O_2$) that is able to eliminate the silicon oxide layer on the glass surface, leaving free hydroxyl groups (—OH) exposed on the surface. The activation process performed on the glass surface is shown in FIG. 11. The reactions on the surface are monitored, amongst other techniques, by measuring the contact angle of a drop of water on the surface obtained after each step. The change in hydrophobicity can be seen by the variation in the contact angle thereof, which decreases from 48.1° for the non-activated surface to 27.3° for the activated surface, the hydrophilicity of which is increased by the presence of exposed hydroxyl groups on the surface.

Each surface-modification step is also characterised by X-ray photoelectron spectrometry (XPS) analysis, which allows us to obtain the atomic concentration of the elements present at the surface to an analytical depth of approximately 5 nm. The present technique is also able to provide information regarding the chemical state of the elements present. A high proportion of Si and O, together with small proportions of C and other elements present as contaminants, is observed for the glass surfaces. The proportion of Si on the activated surface decreases slightly, and that of O increases, along with a small decrease in environmental C (table 13).

presence of an N 1 s peak, which is not present for the starting glass surface, or for the surface activated using piranha solution, is observed at 397 eV (table 13), and the proportion of C increases to exceed that due to possible environmental contamination.

Finally, the surface functionalised with alkynyl groups is formed by amidation of the amino groups present on the surface with pentynoic anhydride, which bears terminal alkynyl groups, in a reaction catalysed by a base such as triethylamine (FIG. 11).

It can be seen from FIG. 11, which shows the reaction steps performed, that contact angle measurements were performed for a drop of water on the surfaces obtained after each step. Said measurements allowed us to study the changes in surface hydrophobicity and therefore served as an initial method for controlling or monitoring each reaction step. Thus, the hydrophobicity of the surface functionalised with alkynyl groups decreases slightly with respect to that for the amino-functionalised surface, as seen from the decrease in contact angle to 64.5° for the former.

The alkynyl-functionalised surface is more extensively coated than the amino-functionalised surface, as seen from the decrease in the proportion of Si 2 p in the XPS analysis. Moreover, a decrease in the proportion of O and a higher relative proportion of C and N is observed, thereby confirming addition of the alkynyl group (table 13).

Additional information concerning the molecular structure of the graft is obtained upon comparing the high-resolution spectra of the various regions of interest. It is possible to identify the different oxidation states of the elements to be studied by deconvoluting the corresponding spectra. A single peak, corresponding to the amino group, can be seen at 399.5 eV in the high-resolution spectrum of the N 1 s region for the aminosilanated surface. The spectrum for the alkynylsilanated surface shows a second nitrogen peak at 401.7 eV corresponding to the nitrogen of the amide group, which is in a higher oxidation state, thus confirming the formation of an amide-type covalent bond. The proportion of the two N peaks for the different oxidation states observed allows us to deduce, by deconvolution, that 30% coupling with alkynyl groups has occurred, a sufficient

TABLE 13

XPS results for the glass surfaces, glass activated with "piranha" solution and amino and alkyne silanised surfaces.

| Peak | GLASS | | GLASS ACTIVATED | | AMINO | | ALKYNE | |
|---|---|---|---|---|---|---|---|---|
| | (eV) | Atom. Conc. (%) | (eV) | Atom. Conc. (%) | (eV) | Atom. Conc. (%) | (eV) | Atom. Conc. (%) |
| C 1s | 285 | 12.1 | 285 | 9.8 | 282 | 33.96 | 283 | 48.24 |
| O 1s | 532 | 41.81 | 532 | 64.4 | 530 | 39.52 | 530 | 25.13 |
| N 1s | 400 | 0.23 | 400 | 0 | 397 | 2.06 | 397 | 8.15 |
| Si 2p | 102 | 29.7 | 102 | 25.8 | 100 | 24.46 | 101 | 18.18 |

The following step comprises obtaining a surface functionalised with amino groups by reaction of the free hydroxyl groups exposed on the recently activated surface with 3-aminopropylsilanol, which is generated "in situ" from 3-aminopropyltrimethoxysiloxane (APTS) (FIG. 11). The routine technique for determining surface modification involves measuring the contact angle of a drop on the surface, with a reasonable increase in hydrophobicity being observed (the contact angle varies from 27.3° for the surface activated with free hydroxyl groups to 78.1° for the surface functionalised with aminopropylsiloxane groups). The surface is also characterised by XPS analysis. The presence of the aminopropyl group is confirmed by said analysis, as the proportion for subsequent functionalisation of the surface with protein-based polymers without being excessive.

The ToF-SIMS analysis for the amino- and alkynyl-functionalised surfaces shows similar spectra in both cases, with said spectra differing from that observed for the non-functionalised surface mainly as regards the ions with mass 23 ($Na^+$), 30 ($CH_4N^+$) and 45 ($CH_3NO^+$) (table 14). The lower intensity for the $Na^+$ ion again allows us to deduce a more extensive coating of the amino- and alkynyl-functionalised surfaces. In addition, two new ions that are not present for the non-functionalised surfaces, namely an ion with mass 30 ($CH_4N^+$), which appears with higher intensity for the alkynyl sample than for the amino sample, and an ion with mass 45 ($CH_3NO^+$), with a similar intensity for both surfaces, are observed, thus allowing us to deduce an organic composition for the coating.

TABLE 14

ToF-SIMS for the glass and amino- and alkynyl-functionalised surfaces.

| Ion mass | GLASS Inten. | AMINO Inten. | ALKYNE Inten. |
|---|---|---|---|
| 23 ($Na^+$) | 66155 | 13703 | 9006 |
| 30 ($CH_4N^+$) | 658 | 8780 | 8015 |
| 42 ($C_2H_4N^+$) | 4552 | 11616 | 5504 |
| 45 ($CH_3NO^+$) | 1882 | 8736 | 8494 |
| 68 ($C_4H_6N^+$) | 1344 | 544 | 1087 |

Figure 14:
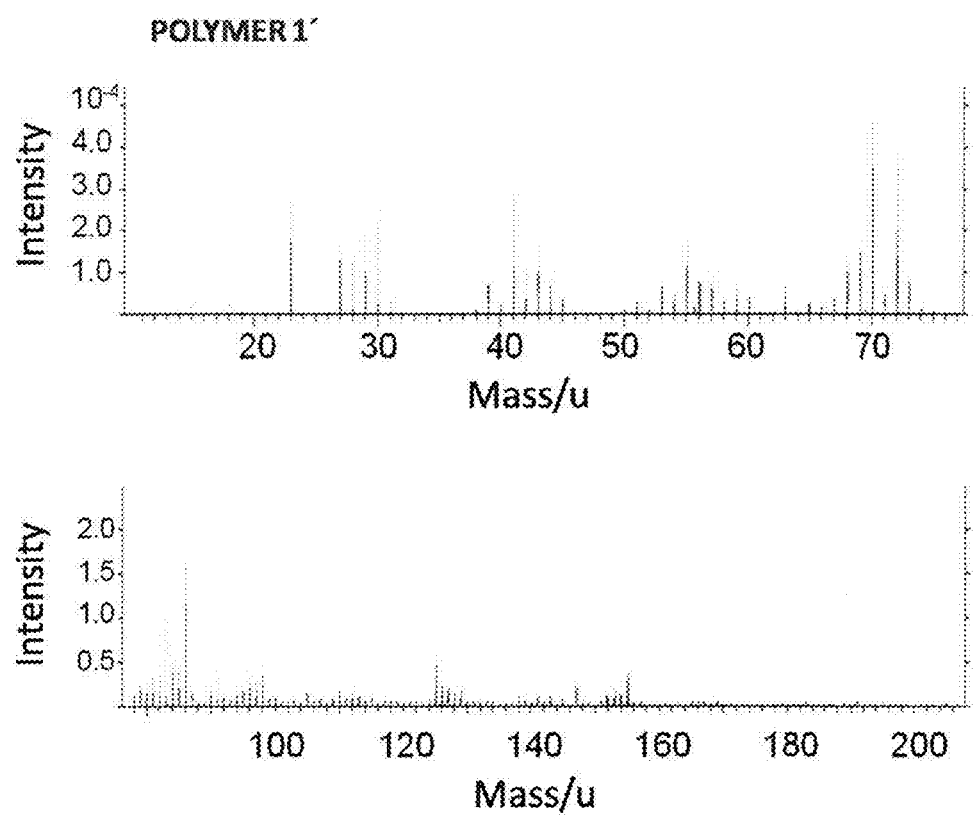
FIG. 14. Time-of-Flight Secondary Ion Mass Spectrometry (ToF-SIMS) analysis of the surface functionalised with polymer 1'. Ions with a mass of 68 ($C_4H_6N^+$) and 72 ($C_4H_{10}N^+$), typical of the presence of an amino acid coating containing valine, 70 ($C_4H_8N^+$), typical of the presence of an amino acid coating containing proline and 86 ($C_5H_{12}N^+$), which shows the presence of an amino acid coating containing isoleucine, are observed.

The surfaces with grafted biopolymers 1'-6' have been characterised by XPS. A greater layer thickness and higher coverage is observed for the surface functionalised with biopolymer 1' than for the surfaces obtained previously with amino and alkynyl functional groups as a result of a lower proportion of Si 2 p (4.21%) and higher proportion of C 1 s (atomic concentration of 59.15%) (table 15) in comparison with the amino- and alkynylsilanated surfaces, thereby indicating that the reaction is efficient and the marked presence of biopolymer 1' grafted to the surface as the 59:23:11 proportion is in accordance with the percentage of said elements in said biopolymer. As can be seen from table 14, a similar behaviour is found for the other surfaces biofunctionalised with polymers 2'-6' analysed. As an example, FIG. 14 shows the XPS analysis of the various surface-functionalisation steps until the surface functionalised with biopolymer 1' is obtained.

TABLE 15

XPS of the surfaces functionalised with polymer 1', polymer 2', polymer 3', polymer 4 adsorbed onto grafted polymer 3' (3' + 4), polymer 4', polymer 5' and polymer 6'.

| | POLYM. 1' | | POLYM. 2' | | POLYM. 3' | |
|---|---|---|---|---|---|---|
| Peak | (eV) | Atom. Conc. (%) | (eV) | Atom. Conc. (%) | (eV) | Atom. Conc. (%) |
| C 1s | 284 | 59.15 | 284 | 69.99 | 284 | 64.24 |
| O 1s | 529 | 23.19 | 529 | 15.29 | 529 | 18.18 |
| N 1s | 398 | 11.16 | 398 | 8.65 | 398 | 9.1 |
| Si 2p | 101 | 4.21 | 101 | 5.18 | 101 | 6.59 |

| | POLYM. 3' + 4 | | POLYM. 4' | | POLYM. 5' | | POLYM. 6' | |
|---|---|---|---|---|---|---|---|---|
| Peak | (eV) | Atom. Conc. (%) | (eV) | Atom. Conc. (%) | (eV) | Atom. Conc. (%) | (eV) | Atom. Conc. (%) |
| C 1s | 284 | 49.62 | 284 | 50.75 | 284 | 54.6 | 284 | 60.25 |
| O 1s | 529 | 20.17 | 529 | 24.87 | 529 | 21.6 | 529 | 25.73 |
| N 1s | 398 | 8.59 | 398 | 8.21 | 398 | 13.5 | 398 | 9.24 |
| Si 2p | 100 | 7.4 | 100 | 16.17 | 100 | 9.19 | 100 | 4.78 |

TABLE 14-continued

ToF-SIMS for the glass and amino- and alkynyl-functionalised surfaces.

| Ion mass | GLASS Inten. | AMINO Inten. | ALKYNE Inten. |
|---|---|---|---|
| 70 ($C_4H_8N^+$) | 898 | 72 | 132 |
| 72 ($C_4H_{10}N^+$) | 1164 | 134 | 100 |
| 86 ($C_5H_{12}N^+$) | 134 | 196 | 219 |

Inten.: intensity.

Biofunctionalisation of the Surfaces by "Click"-Type Cycloaddition

Figure 12:
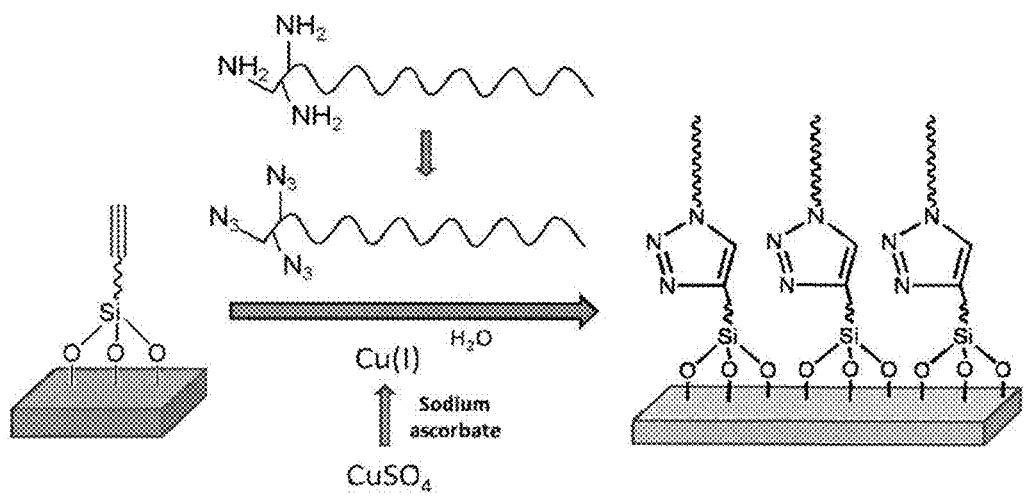
FIG. 12. Scheme showing "click"-type biofunctionalisation of the surface with elastin-like polymers. The 1.3-dipolar cycloaddition reaction between an azide groups and an alkynyl groups generates the corresponding 1,4-disubstituted 1,2,3-triazole in a reaction in an aqueous medium catalysed by the Cu(I) ion generated "in situ" by reduction of Cu(II) in the presence of ascorbate.
Figure 13:
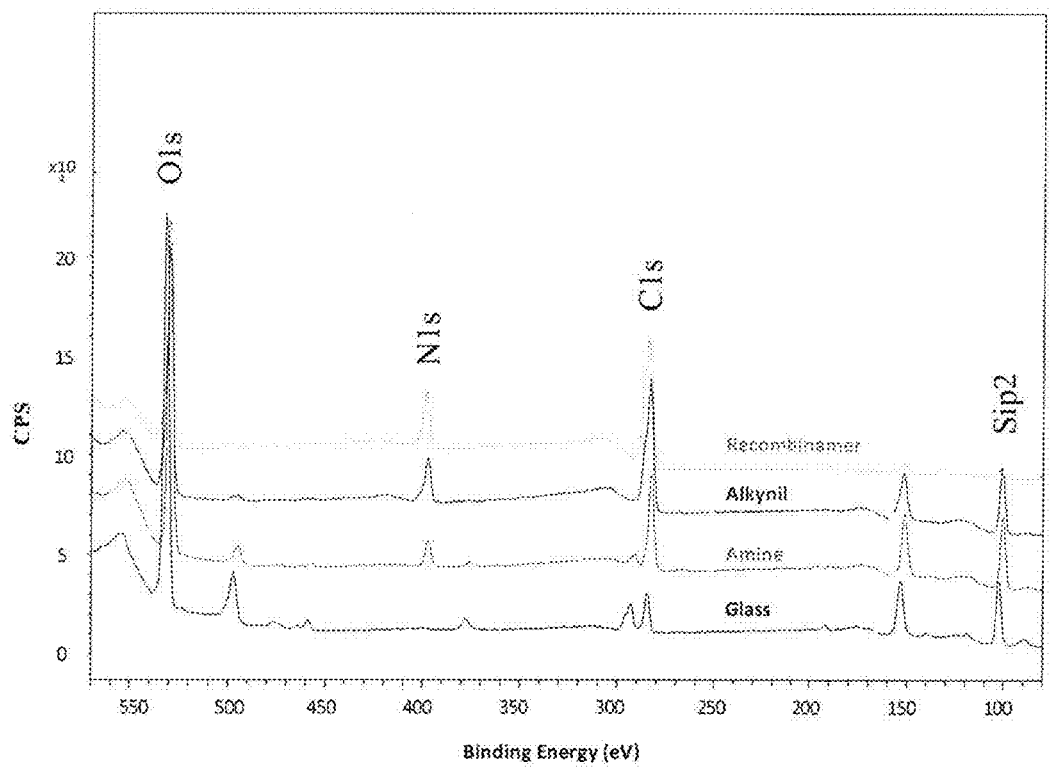
FIG. 13. Comparative X-ray photoelectron spectrometric (XPS) analysis of glass and the surfaces functionalised with amino groups, alkynyl groups and polymer 1'. A more extensive coating of the surface to which the polymer is covalently bound can be deduced from the lower proportion of silicon than for the other three samples. Moreover, the proportion of nitrogen is seen to increase for the treated surfaces with respect to the original glass. This is to be expected due to the nitrogen content of the amino and amide groups in the sampled functionalised with amino and alkyne groups and in the biofunctionalised samples.

The modified biopolymers 1'-6' have been covalently bound to the surface functionalised with alkynyl groups by a "click"-type cycloaddition reaction between the azide groups of the polymers and the alkynyl groups exposed on the surface (FIG. 12).

The formation of a 1,4-disubstituted 1,2,3-triazole occurs upon Hüisgen-type 1,3-dipolar cycloaddition in an aqueous medium catalysed by the Cu(I) ion, which is generated "in situ" by reduction of the Cu(II) ion in the presence of ascorbate. This type of reaction occurs under mild conditions, is highly tolerant of water, oxygen and other functional groups that may be present, and can be carried out in a wide range of protic and aprotic solvents, giving high yields (FIG. 12).

ToF-SIMS spectroscopic analyses for the surfaces grafted with modified polymers 1'-6' show a spectrum that differs from that observed for the amino- and alkynyl-functionalised surfaces, said spectrum suggesting the presence of a protein-based coating due to the presence of the typical ions produced by the amino acids valine, proline, isoleucine and glycine. As an example, FIG. 14 shows the ToF-SIMS analysis for the surface functionalised with polymer 1'. Said FIG. shows ions with a mass of 68 ($C_4H_6N^+$) and 72 ($C_4H_{10}N^+$), typical of the presence of an amino acid coating containing valine, 70 ($C_4H_8N^+$), typical of the presence of an amino acid coating containing proline and 86 ($C_5H_{12}N^+$), which shows the presence of an amino acid coating containing isoleucine. None of the aforementioned peaks are present for the surface functionalised with alkynyl groups, thus corroborating a protein-based coating on the new surfaces grafted with polymer 1'. A similar behaviour is observed for all surfaces studied with the exception of the surface biofunctionalised with polymer 3', for which the absence of isoleucine amino acids results in a lower proportion of the ion with a molecular weight of 86 (table 16). It should be noted that the presence of an ion with mass 86 for the system 3'+4 shows the efficient adsorption of polymer 4 onto the surface grafted with polymer 3'.

TABLE 16

ToF-SIMS for the surfaces functionalised with polymer 1', 2', 3', 4, 3' + 4, 4', 5' and 6'.

| | POLYM. 1' | POLYM. 2' | POLYM. 3' | POLYM. 3' + 4 | POLYM. 4' | POLYM. 5' | POLYM. 6' |
|---|---|---|---|---|---|---|---|
| Ion mass | I | I | I | I | I | I | I |
| 23 ($Na^+$) | 22442 | 8555 | 1897 | 12747 | 7555 | 36885 | 7554 |
| 30 ($CH_4N^+$) | 16977 | 13366 | 34745 | 18046 | 15230 | 33629 | 15440 |
| 42 ($C_2H_4N^+$) | 5039 | 4078 | 11670 | 5032 | 6025 | 7065 | 5778 |
| 45 ($CH_3NO^+$) | 2048 | 1947 | 9890 | 4224 | 2200 | 2168 | 3474 |
| 68 ($C_4H_6N^+$) | 8562 | 6397 | 19439 | 6172 | 8324 | 13359 | 8418 |
| 70 ($C_4H_8N^+$) | 23383 | 21665 | 22179 | 32149 | 21535 | 46895 | 24335 |
| 72 ($C_4H_{10}N^+$) | 21709 | 21179 | 34054 | 14888 | 20214 | 33960 | 27004 |
| 86 ($C_5H_{12}N^+$) | 9390 | 6617 | 1999 | 6553 | 7550 | 22150 | 35714 |

I: intensity.

XPS (table 15) and ToF-SIMS analysis (table 16) of the surface grafted with biopolymer 4' indicates that the reaction is not efficient with a single terminal amino group and that the surface does not exhibit an adequate coating of grafted biopolymer 4', as deduced from the results obtained using said techniques, which show the presence of a high proportion of Si 2 p on the surface (16.17%) together with a lower proportion of C 1 s (50.75%).

XPS (table 15) and ToF-SIMS analysis (table 16) of the surfaces grafted with biopolymers 5' and 6' indicates that the reaction is efficient, that there is a marked quantity of biopolymer present on the surface and that the coating of both biopolymer 5' and biopolymer 6' is adequate. To check whether the smart behaviour of the biopolymers is retained when said biopolymers are grafted onto surfaces, and therefore that such systems are viable as cell-harvesting systems, contact angle measurements have been performed for heat-treated samples. Measurements were performed above (at 37° C.) and below the transition temperature (at 10° C.), with the values shown in table 17 being obtained at said temperatures.

Different contact angles of 76.8±1.2° and 65.2±0.8° were obtained for the surface functionalised with biopolymer 1' at 10° C. and 37° C., respectively, as a result of the different folding of the structure of said biopolymer. It can be seen that the hydrophobicity of the surface is greater above the transition temperature of the biopolymer. This is due to the fact that the polymer passes from a hydrated state to a non-hydrated state when the transition temperature (Tt) is exceeded, in other words the hydrophilic character thereof decreases with temperature. The results are shown in table 17.

TABLE 17

Contact angles for the surfaces functionalised with polymers 1'-6' at different temperatures.

| SURFACE | ANGLE at 10° C. | ANGLE at 37° C. | ΔT |
|---|---|---|---|
| Polymer 1' | 65.2 ± 0.8° | 76.8 ± 1.2° | 11.6° |
| Polymer 2' | 65.9 ± 1.0° | 74.9 ± 0.7° | 9.0° |
| Polymer 3' | 59.7 ± 2.1° | 64.8 ± 1.1° | 5.1° |
| Polymer 3' + 4 | 49.0 ± 1.9° | 53.2 ± 4.2° | 4.2° |
| Polymer 4' | 60.3 ± 0.5° | 64.1 ± 1.5° | 3.8° |

TABLE 17-continued

Contact angles for the surfaces functionalised with polymers 1'-6' at different temperatures.

| SURFACE | ANGLE at 10° C. | ANGLE at 37° C. | ΔT |
|---|---|---|---|
| Polymer 5' | 67.5 ± 0.7° | 65.3 ± 0.6° | 2.4° |
| Polymer 6' | 43.5 ± 1.2° | 49.1 ± 2.0° | 5.6° |

The limited coating of the surface with polymer 4' can again be seen from the small decrease in the contact angle for the surface functionalised with said polymer 4', this angle only varying by 3.8° for the surface at 10° C. (60.3±0.5°) and 37° C. (64.1±1.5°). As the structure of polymer 4' is completely analogous to that of polymer 1', the small variation observed suggests the limited presence of polymer on the surface, thus meaning that similar values to those found for the non-grafted surface coated with alkynyl groups (64.5°, FIG. 11) are found.

The contact angle measurements performed for the surface biofunctionalised with biopolymer 5' (table 17) show that the hydrophobicity of said surface varies markedly with temperature, with values of 65.3±0.6° at 37° C. and 67.5±0.7° at 10° C. These values show that as polymer 5' is covalently bound to the surface at various points along the polymer chain, said polymer does not have the required freedom of movement to change its conformation with temperature and therefore that it may lose its ability to be used as a cell-harvesting system.

Although the smart behaviour of biopolymer 6' is maintained on the surface, as can be deduced from the contact angle measurements performed on the surface (table 17), with a decrease in surface hydrophobicity again being observed upon decreasing the temperature below the transition temperature, from 49.1±1.2° at 37° C. to 43.5±2.0° at 10° C., the values observed confirm the grater hydrophilicity of grafted polymer 4' due to the presence of the three polar RGD cell-adhesion sequences Biofunctionalisation of Surfaces by "click"-Type Cycloaddition of Polymer 3' and Subsequent Adsorption of Polymer 4

A system comprising two biopolymers, the first of which (polymer 3) is able to graft to the surface and the second of which (polymer 4) is able to induce cell adhesion such that the system is useful as a cell-harvesting system due to the synergy between the effects of each polymer.

The bioactive RGD sequence in polymer 4 induces cell adhesion to the bioactive surface at temperatures above the inverse transition temperature coincident with the cell culture temperature.

Peptide B, which is included in polymer 4 as a carrier of the smart properties of the polymer, prevents cell adhesion below the inverse transition temperature, thereby nullifying the effect of the more polar regions that favour cell adhesion.

Modified biopolymer 3' was covalently bound by a chemical "click"-type cycloaddition reaction between the azide groups of the polymer and the alkynyl groups present on the surface. The procedure was the same as that described for polymers 1' and 2'.

Once the surfaces biofunctionalised with chemically grafted polymer 3' had been obtained, polymer 4 was adsorbed onto said polymer 3' by immersing the previously prepared surfaces in an aqueous solution of biopolymer 4. The surface functionalised with biopolymers 3' and 4 was characterised by XPS, which showed a greater layer thickness and more extensive coating than for the surfaces functionalised with amino and/or alkynyl groups, as deduced from the lower proportion of Si 2 p and the higher proportion of C 1 s (table 15) found for the surfaces biofunctionalised with polymer 4 in comparison with the amino- and alkynylsilanated surfaces, thereby indicating an important presence of biopolymers on the surface.

Example 4

Cell Adhesion Assays

Study of the Cell-Harvesting Process Using Bioactive Surfaces

The study of the cell-harvesting process using this type of surface was divided into two parts: the harvesting of individual cells and the harvesting of a cell sheet using polyvinylidene fluoride (PVDF) membranes.

Harvesting Individual Cells

Figure 15:
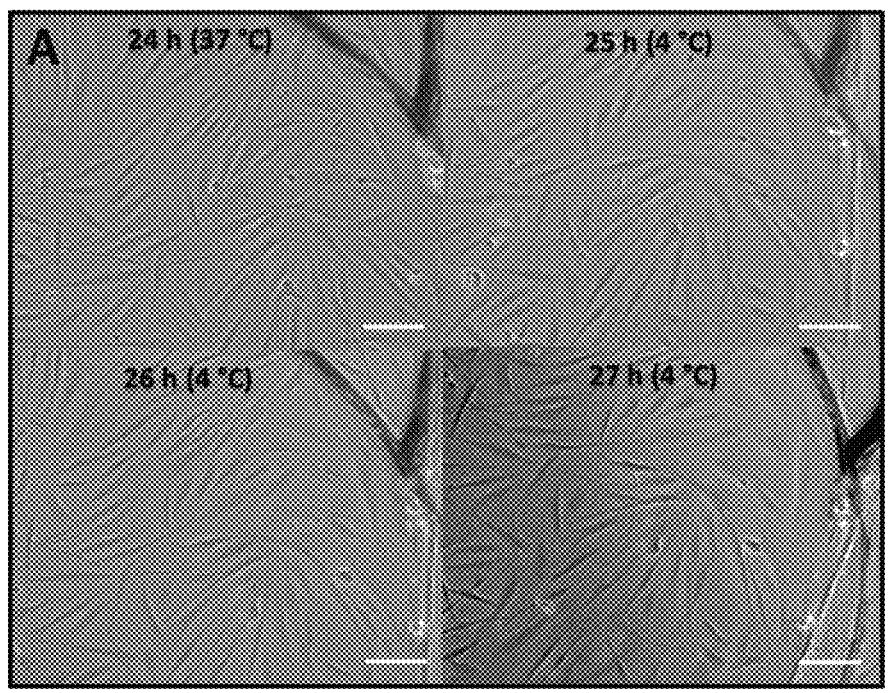
FIG. 15. Phase-contrast optical microscopy images (magnification: ×10) of the same field at 24 h, 25 h, 26 h and 27 h for the 8 different surfaces: A) glass, B) polymer 1', C) polymer 2', D) polymer 3', E) polymers 3'+4, F) polymer 4', G) polymer 5', H) polymer 6'. The scale bar corresponds to 100 micrometers.
Figure 15:
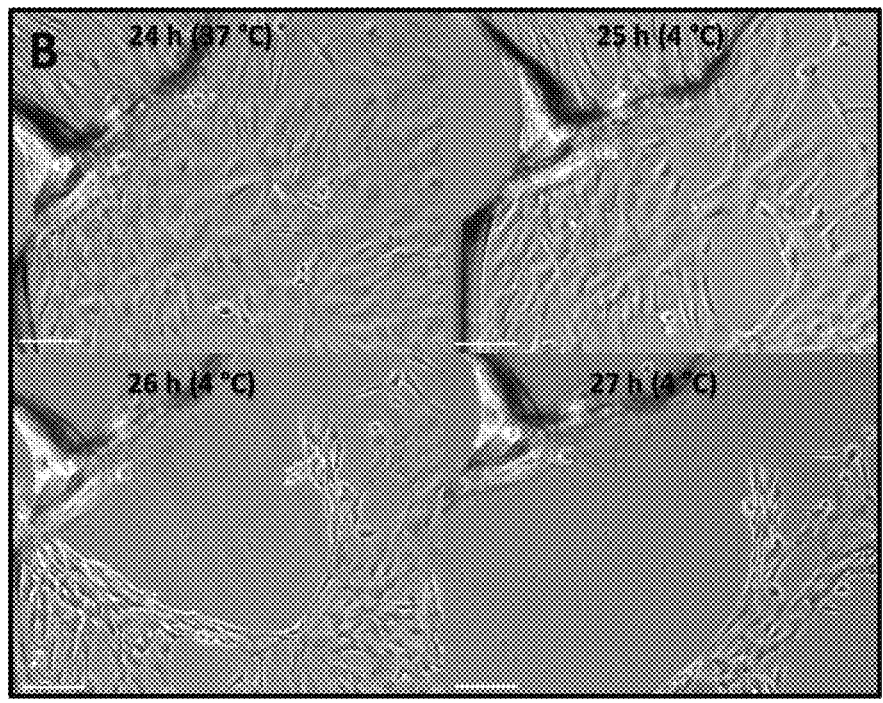
Figure 15:
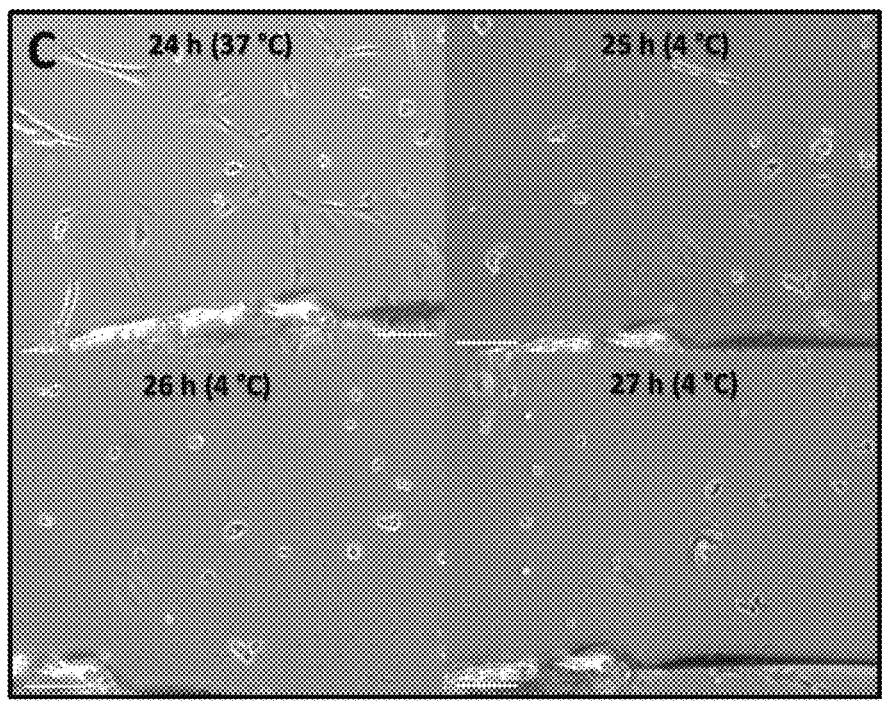
Figure 15:
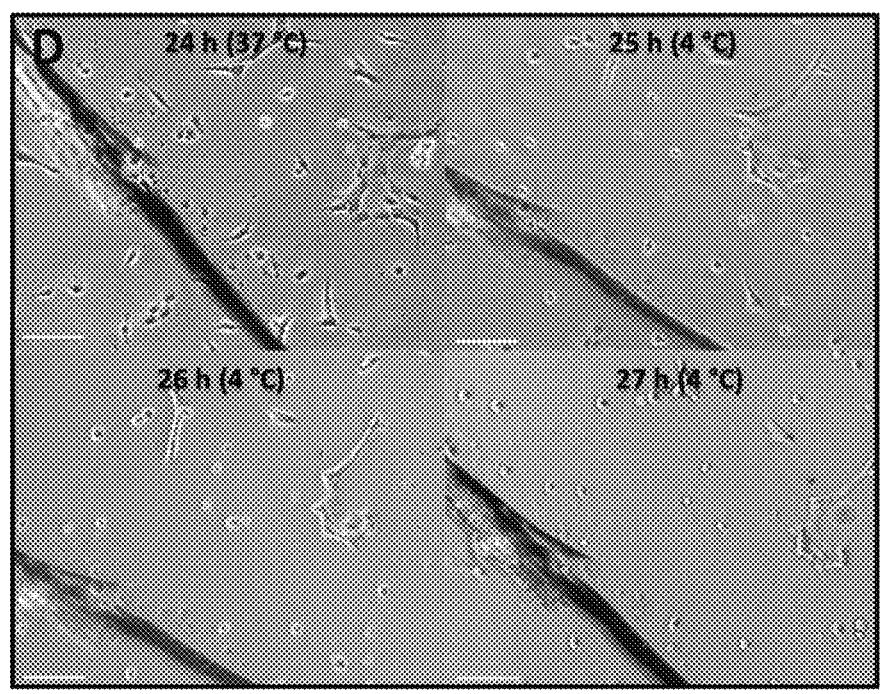
Figure 15:
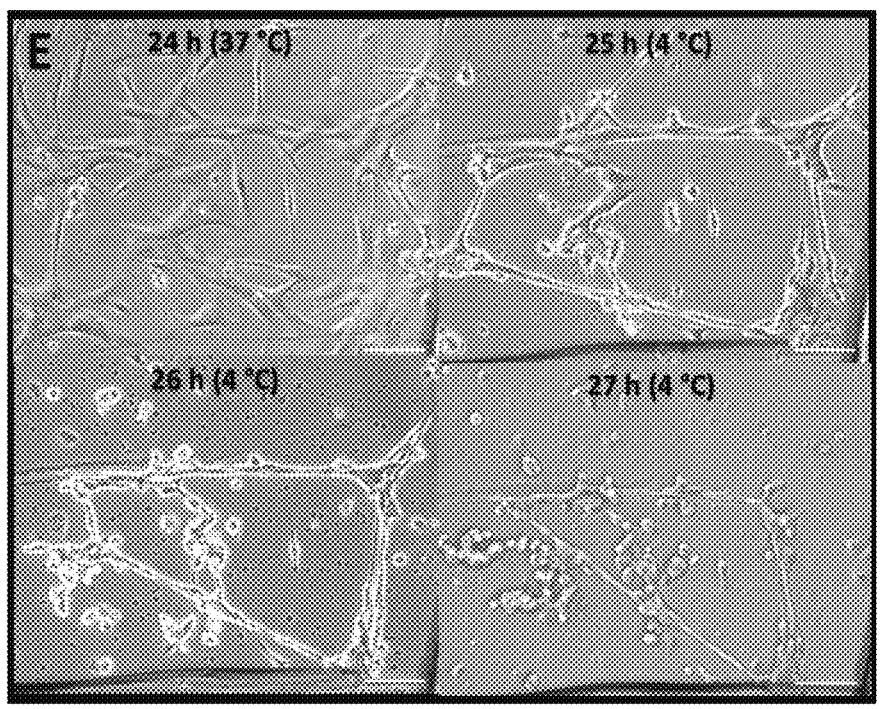
Figure 15:
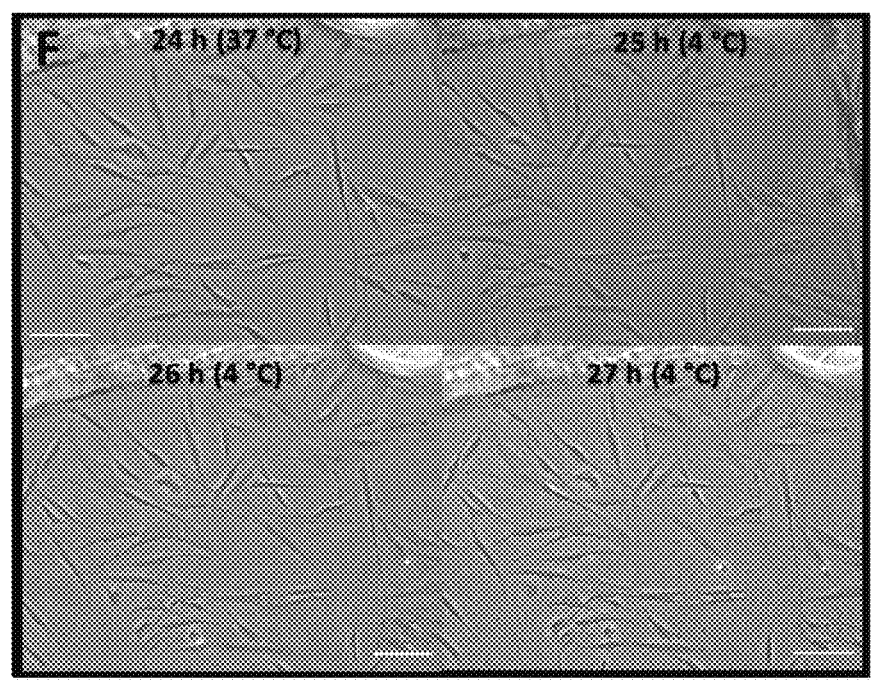
Figure 15:
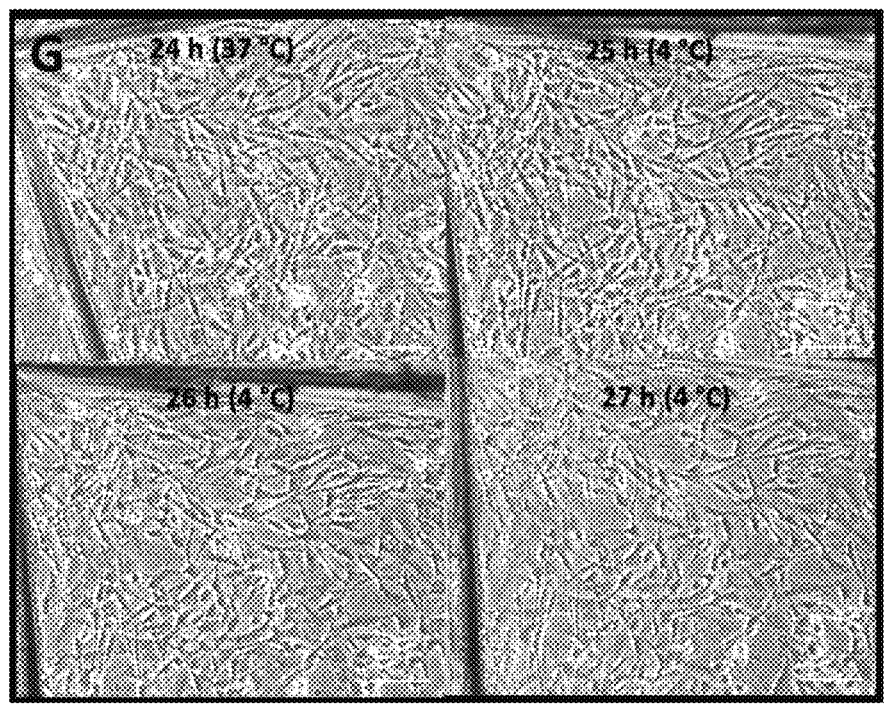
Figure 15:
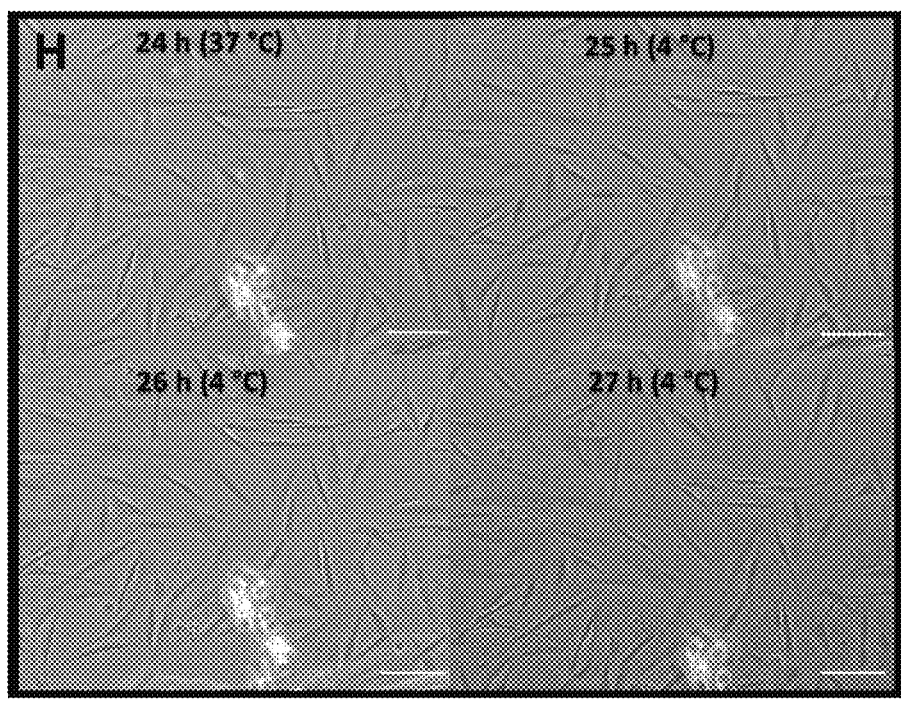

The surfaces biofunctionalised with the elastin-like polymer are sterilised under UV light for 30 minutes each side. In addition, the wells of the 24-well multiwell polystyrene plates are treated with 0.1% bovine serum albumin (BSA) in PBS and maintained overnight at 4° C. to prevent the cells from binding non-specifically. The plates are then washed three times with PBS and the sterile biofunctionalised surfaces placed in the corresponding wells. Human fibroblasts (HFF-1 cell line) are also seeded separately. Said fibroblasts are cultured at 37° C. in 250 mL flasks containing Dulbecco's Modified Eagle Medium (DMEM) supplemented with 15% foetal bovine serum (FBS) and 1% penicillin-streptomycin at a concentration of 5% $CO_2$ in air. Once the cells have achieved confluence, they are harvested by treatment with 0.25% trypsin and 0.02% ethylenediaminetetraacetic acid (EDTA) in PBS. After centrifugation of the resulting cell suspension, said cells are resuspended in DMEM supplemented with 1% penicillin-streptomycin. The cell suspension is diluted to $2\times10^4$ cells/well and 500 µL aliquots added to each of the biofunctionalised surfaces in the wells and incubated at 37° C. at a concentration of 5% $CO_2$ in air. Cell morphology is assessed and photographed at 30 minutes and 4, 8 and 24 hours (h) (FIG. 15) post-seeding by phase-contrast using an optical microscope equipped with a digital camera system. Each experiment is repeated four times under the same conditions, assessing three repeats of each experiment and analysing the cells in 9 randomly selected fields on each surface using the photographs obtained.

After culture for 24 h, the multiwell plates containing surfaces with adhered cells are cooled to 4° C. After incubation for a further hour (25 h since the start of the experiment), 2 h (26 h since the start of the experiment) and 3 h (27 h since the start of the experiment), the cell morphology is observed and photographed as indicated above, considering rounded cells not to be adhered and extended cells to be adhered (FIGS. 16 and 17).

The percentage of adhered cells and the total number of adhered cells is given as the mean value (n=4) and standard deviation thereof. Non-biofunctionalised glass surfaces free from any type of coating are used as adhesion and harvesting controls.

Figure 16:
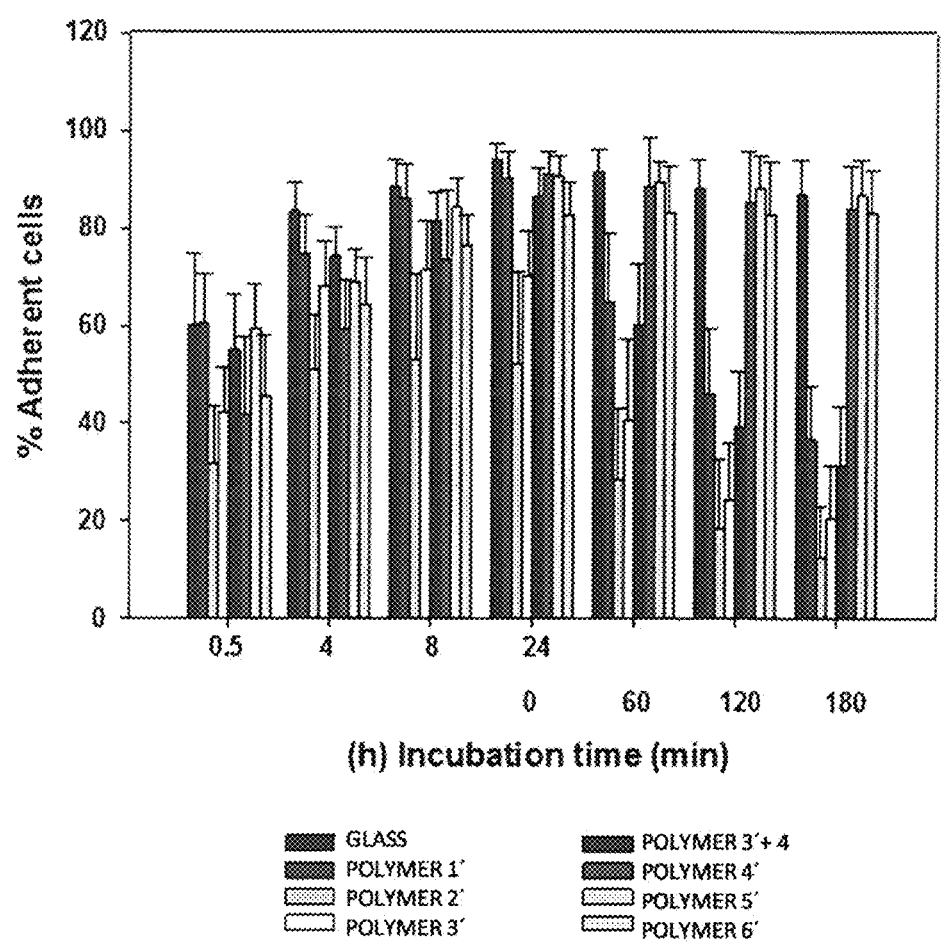
FIG. 16. Evaluation of the percentage of cells adhered with respect to the total with time for 9 random fields from three samples repeated in four independent experiments for the various surfaces.
Figure 17:
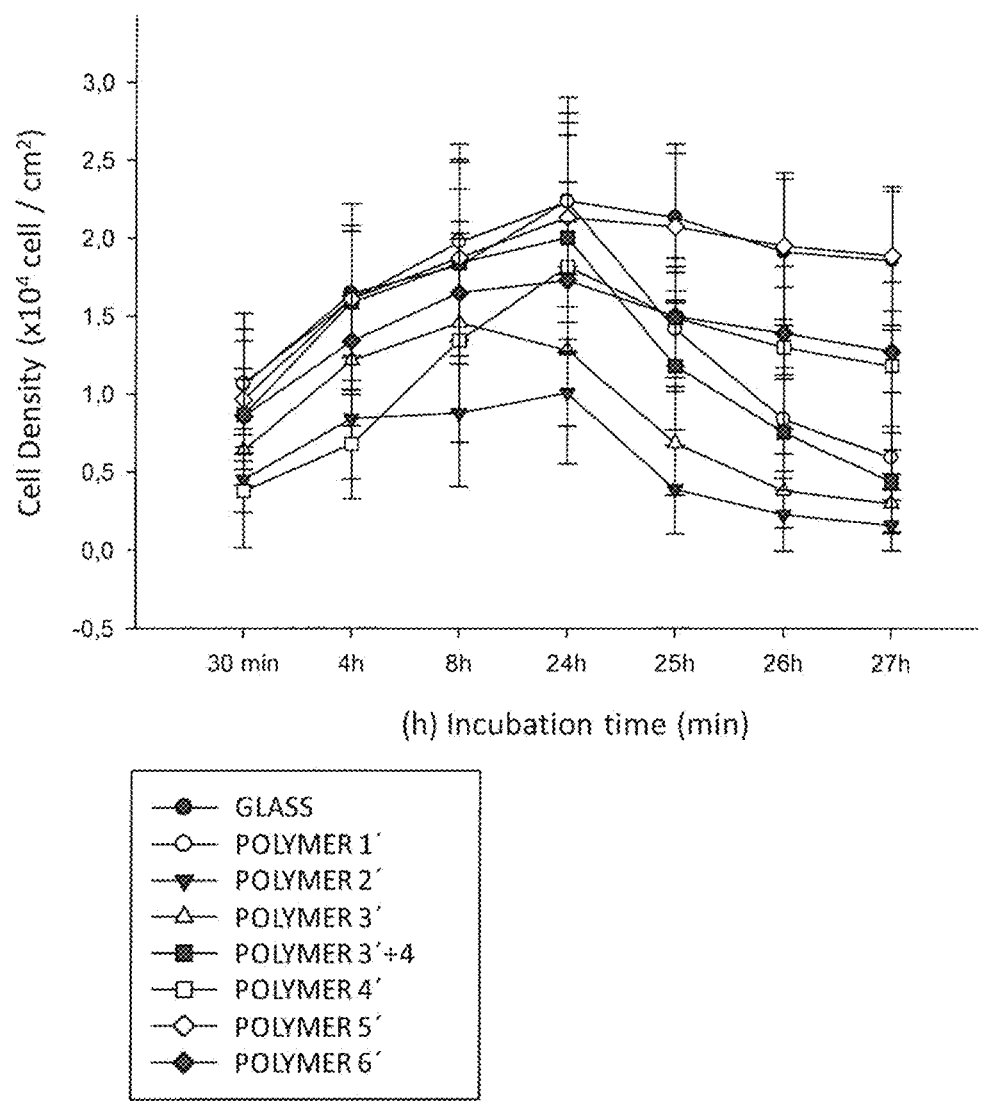
FIG. 17. Evaluation of the total number of cells adhered and not adhered with time for 9 random fields from three samples repeated in four independent experiments for the various surfaces.

The surface functionalised with modified biopolymer 1' shown in FIG. 15B, which contains the bioactive RGD peptide sequence, shows very good adhesion at 30 minutes, similar to that of glass (FIGS. 16 and 17). At 24 h this adhesion continues to be similar to that for the glass surface in terms of percentage and number of cells, as can be seen from the images of the extension and cell morphology (FIG. 15B).

However, in contrast to the uncoated glass surfaces, it can be seen that when the temperature decreases below the Tt for the polymer the cells begin to detach, with large inter-cell spaces appearing, and said cells begin to acquire a more rounded morphology (FIG. 15B).

Thus, the number of cells adhered decreases from 24 h onwards and a large increase in the number of non-adhered cells, which correspond to those with a more rounded morphology, is observed. Said cells do not interact with the surface but maintain interactions between each other and with the extracellular matrix. The cells therefore show a high adhesion capacity and a response to the temperature change that causes them to detach. Consequently, when constructing an effective cell-harvesting system the presence of a bioactive cell-adhesion sequence to which the cells can efficiently adhere is just as important as the ability of the polymer grafted to the surface to change conformation with temperature and become non-adherent.

FIG. 15C shows the surface functionalised with modified biopolymer 2' containing the RDG peptide sequence, which is the scrambled version of RGD and in which the adhesion capacity of the latter peptide is nullified. The number of cells able to adhere to this surface is significantly lower than for the glass surface and the surface with polymer 1' (FIG. 15A, B). Moreover, said adhesion is clearly weaker.

The cell morphology after incubation for 24 h shows that very few cells are able to effectively bind to the surface grafted with modified biopolymer 2'. This results in rapid detachment in the event of a temperature change (FIG. 17), as can be seen from the photograph corresponding to incubation for 25 h (FIG. 15C). Said surface therefore shows a poor adhesion capacity but retains the smart response to a temperature change inherent to elastin-like polymers, although is insufficient for the construction of an effective harvesting system (FIG. 16).

The surface in FIG. 15F corresponds to a surface functionalised with modified biopolymer 3', which lacks a bioactive peptide sequence. The number of cells able to adhere to this surface is significantly lower than for the glass surface and the surface grafted with modified biopolymer 1'. Moreover, cell adhesion to the surface functionalised with modified biopolymer 3' is labile. The cell morphology after incubation for 24 h shows that the number of cells able to effectively bind to the surface is low (FIG. 16). This low and ineffective adhesion results in rapid cell detachment from the surface in the event of a temperature change, as can be seen from the photograph corresponding to incubation for 25 h in FIG. 15D and FIG. 17. Consequently, said surface shows a low cell adhesion capacity, thus meaning that it constitutes an ineffective cell-harvesting system despite maintaining the smart response to a temperature change inherent to elastin-like polymers.

FIG. 15E shows surfaces functionalised with modified biopolymer 3' on which biopolymer 4, which contains the bioactive RGD peptide sequence, is adsorbed. This two-polymer system shows very good cell adhesion at 30 minutes, although said adhesion is lower than that for glass and for the surface functionalised with polymer 1', as can be seen from FIGS. 16 and 17. Cell adhesion to the surface functionalised with modified biopolymer 3' to which biopolymer 4 is adsorbed remains significantly lower at 24 h, although the cells preserve a similar morphology (FIGS. 15E and 17). In stark contrast to the glass surface, a decrease in temperature to below the Tt for the polymer causes the cells to begin to detach and acquire a more rounded morphology. Thus, from 24 h onwards, the number of cells adhered decreases and the number of cells not adhered, with a rounded morphology, increases markedly. These cells continue to interact with each other and with the extracellular matrix, but not with the surface. In light of the images and drawings, the cells therefore show a high adhesion capacity and a response to the temperature change that causes them to detach. This could be an effective system for cell harvesting, although not as effective as the system comprising polymer 1', which, as well as being effective for both cell adhesion and detachment upon heat treatment (FIGS. 15B and 16), only requires the presence of a single polymer grafted to the surface. Moreover, it should be considered that, in contrast to the example with polymer 1', in which no residues are washed out due to covalent bonding of the biopolymer to the surface, the cells harvested from this surface would contain traces of polymer 4. A further drawback of the system comprising grafted biopolymer 3' and adsorbed biopolymer 4 is the fact that polymer 4 is only adsorbed, which could result in non-specific release into the medium during cell culture.

The surface functionalised with modified biopolymer 4', which contains the bioactive RGD peptide sequence but does not present lysine residues at the terminus thereof, is shown in FIG. 15F. Said polymer 4' can be grafted to the surface once the terminal amino groups thereof have been modified, although it is observed that modification of the terminal amino group of the biopolymer only is insufficient to ensure complete coating of the treated surface. This surface shows poor cell adhesion at 30 minutes as the insufficient coating of the glass surface means that cells have to adhere to the exposed regions of glass functionalised with alkynyl groups, where adhesion is ineffective. As a result, subsequent detachment of the cells upon heat treatment is ineffective and said cells remain adhered to the surface (FIGS. 16 and 17). The limited efficiency of the coupling of biopolymer 4' to the surface makes use of said biopolymer for the construction of a cell-harvesting system unfeasible.

This finding shows that the connection between the biopolymer and the scaffold must involve at least two covalent bonds per biopolymer molecule, more preferably three covalent bonds per biopolymer molecule. Consequently, these results corroborate those obtained previously for this surface when measuring the contact angles (table 17), which indicated a lower surface coating when biopolymer 4' was used as no major change was observed with temperature.

As can be seen from FIG. 15G, the surface functionalised with modified biopolymer 5', which contains 24 lysine residues and six repeats of the bioactive RGD peptide sequence throughout the amino acid chain, shows very good cell adhesion at 30 minutes, similar to that observed for glass and biopolymer 1'. This adhesion continues to be comparable to that obtained for the glass surface, in terms of both surface coating and cell morphology, at 24 h, as can be seen from the images (FIG. 15G).

However, it can be seen that the cells do not detach from the surface of the substrate upon decreasing the temperature below the Tt for biopolymer 5'. This implies that binding of the biopolymer via residues located throughout the molecule does not allow a conformational change upon decreasing the temperature, as confirmed by the invariability of the contact angle on said surface (table 17). Biopolymer 5' is therefore not useful for constructing an effective cell-harvesting system, thereby again demonstrating that the presence of a bioactive cell-adhesion sequence to which the cells can efficiently adhere is just as important as the ability of the polymer grafted to the surface to conserve its ability to change conformation with temperature. Binding to the surface via various points along the peptide skeleton of biopolymer 5' does not allow the necessary conformational change in the biopolymer for the cells to detach. In conclusion, biopolymer 5' is also not useful for the construction of a cell-harvesting system.

As can be seen from FIG. 15H, the surface functionalised with modified biopolymer 6', which contains the bioactive RGD peptide sequence repeated three times throughout the amino acid chain along with three lysine residues at the amino-terminus, exhibits similar adhesion to that obtained for glass after incubation for 30 minutes. This adhesion remains comparable in terms of both area covered and cell morphology after 24 h (FIGS. 15H and 17). However, it can be seen that the cells do not detach from the surface of the substrate upon decreasing the temperature below the Tt for said biopolymer (FIG. 17). This implies that the presence of various bioactive RGD sequences throughout the peptide chain does not allow an appropriate conformational change in the molecule that can cause mass detachment of the cells, with some portion of the RGD sequence likely remaining exposed in the new conformation, said portion being sufficient to allow the cells to remain adhered. This finding is in agreement with the limited change in the contact angles on this surface with temperature (table 17). Biopolymer 6' is therefore not useful for cell harvesting or for the construction of an effective cell-harvesting system. Therefore, it has again been demonstrated that the presence of a bioactive cell-adhesion sequence to which the cells can efficiently adhere is just as important as the ability of the polymer grafted to the surface to change its conformation in an appropriate manner, exposing the bioactive sequence to cells, or not, depending on the temperature.

After 3 hours at 4° C. (27 h from the start of the experiment), the viability of the cells present on the surfaces was assessed using the "Live-Dead cell staining kit" (Abeam) fluorescence technique. Live, or green-coloured, cells and dead, or red-coloured cells, were counted in 9 photographs corresponding to different random regions on each surface. The percentage of live cells is calculated along with the corresponding standard deviation (n=4).

In this experiment it was confirmed that, after heat treatment, the cells present on the surfaces biofunctionalised with modified polymers 1', 2', 3', 3'+4, 5' and 6' exhibit viability percentages higher than 90% (table 18) in all cases, thereby demonstrating that culture on the biopolymers and heat treatment have no adverse effects on cell viability.

TABLE 18

Cell viability as assessed using the "Live-Dead cell staining kit" fluorescence technique.

| Material | % Live cells | Standard Deviation |
|---|---|---|
| GLASS | 99.15 | 1.33 |
| (POLYMER 1') | 99.38 | 0.97 |
| (POLYMER 2') | 97.68 | 4.00 |
| (POLYMER 3') | 97.41 | 1.79 |
| (POLYMERS 3' + 4) | 90.08 | 4.02 |
| (POLYMER 4') | 98.54 | 1.52 |
| (POLYMER 5') | 95.42 | 2.34 |
| (POLYMER 6') | 97.38 | 3.41 |

The vitality of the fibroblasts detached after culture on surfaces functionalised with modified polymer 1' for 27 h has also been assessed. Thus, the fibroblasts attached are analysed by culture at 37° C. on TC polystyrene plates for 1, 3, 10 and 14 days at a concentration of 5% $CO_2$ in air using the "Alamar Blue" colorimetric technique. The same number of fibroblasts, obtained using the trypsinisation technique, cultured at 37° C. on the same TC polystyrene plates for 1, 3, 10 and 14 days at a concentration of 5% $CO_2$ was used as control. The experiment is repeated four times, under the same conditions, evaluating three repeats in each case.

Figure 18:
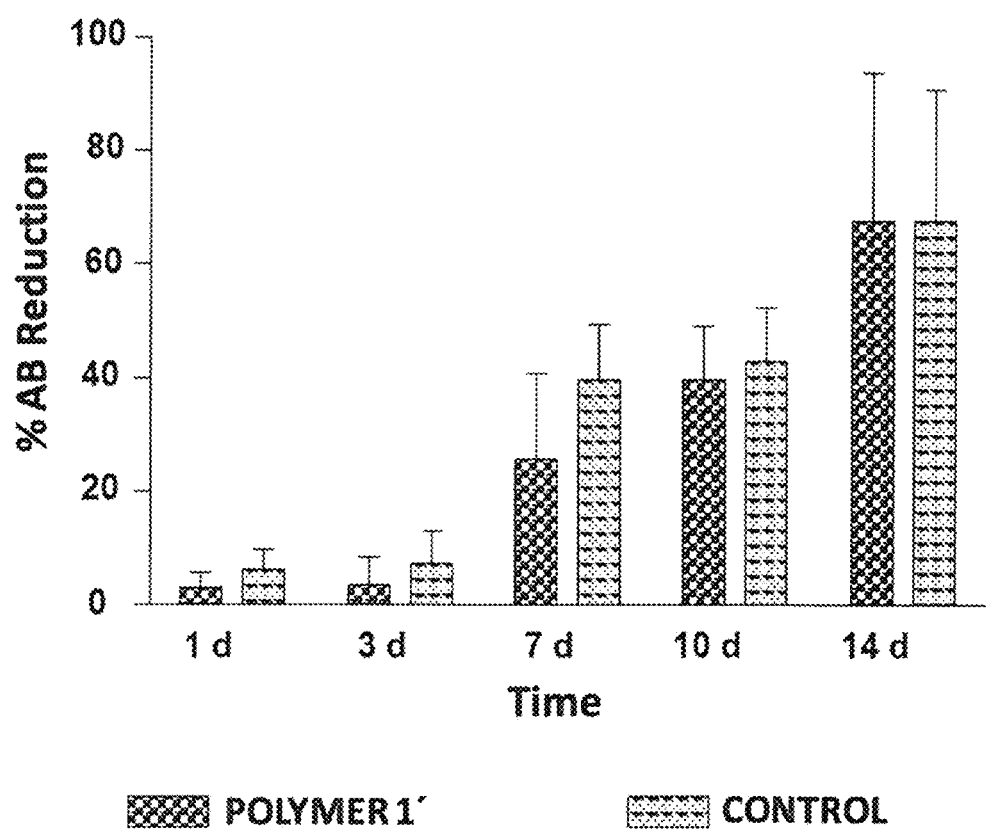
FIG. 18. Evaluation of the cell viability for cells detached from the biofunctionalised surfaces (polymer 1') and freshly trypsinised cells (control) at different incubation times for cells on polystyrene using the "Alamar Blue" colorimetry technique (p<0.05).

The result obtained is a constant increase in metabolic activity with time, with no significant differences with respect to the controls (P<0.05), thus meaning that the cells are viable and able to proliferate (FIG. 18), catching up with the trypsinised fibroblasts with time. This highlights that use of biopolymer 1' is a more effective cell-harvesting method that does not affect the proteins in the cell membrane and therefore maintains the cell-cell and cell-extracellular matrix interactions intact. Moreover, this test again shows that heat treatment has no adverse effects on cell viability.

Harvesting a Cell Sheet Using PVDF Membranes

The glass surfaces biofunctionalised and grafted with biopolymer 1' are sterilised under UV light for 30 minutes each side.

In addition, the wells of the 24-well multiwell polystyrene plates are treated with 0.1% BSA in PBS and maintained overnight at 4° C. to prevent the cells from binding non-specifically. The wells are then washed three times with PBS and the sterilised glass surfaces biofunctionalised and grafted with biopolymer 1' placed in the corresponding wells.

Cell seeding is then performed. HFF-1 fibroblasts are used throughout the experiment. Said fibroblasts are cultured at 37° C. in 250 mL flasks containing DMEM supplemented with 10% FBS and 1% penicillin-streptomycin at a concentration of 5% $CO_2$ in air. Once the cells have achieved confluence, they are harvested by treatment with 0.25% trypsin and 0.02% EDTA in PBS. This enzymatic digestion is quenched by addition of DMEM supplemented with 1% penicillin-streptomycin. The cell suspension is adjusted to $2\times10^4$ cells/well. 500 µL aliquots are added to the glass surfaces biofunctionalised and grafted with biopolymer 1' in each well and incubated at 37° C. at a concentration of 5% $CO_2$ in air until the cells achieve confluence. Once confluence has been achieved in the culture, the culture temperature is decreased to 4° C. After one hour at 4° C., a PVDF membrane is placed in each well. The culture medium is removed by aspiration such that the PVDF membrane adheres to the cell sheet. The plates are again incubated for half an hour at 4° C. After this time, and with the help of tweezers, the PVDF membrane adhered to the cell sheet is transferred to a new polystyrene plate. Said membrane floats upon addition of cold culture medium and is collected using tweezers, leaving only the cell sheet in the well. The good viability of the cells comprising the sheet was confirmed by studying the proliferation thereof qualitatively once transferred to a new culture plate.

The invention claimed is:

1. A biopolymer comprising peptides A, B and D, with the structure [(D-$B_n$-$A_m$-$B_s$)], where A has the structure ($F_{t1}$-G-$F_{t2}$), where D is the peptide SEQ ID No. 4, B is the peptide SEQ ID No. 3, n and s have a value of 14, F is the peptide SEQ ID No. 2, t1 and t2 have a value of 10, G is the peptide SEQ ID No. 1 and m has a value of 2.

2. A nucleic acid comprising a nucleotide sequence that codes for the amino acid sequence of the biopolymer according to claim 1.

3. A cell-harvesting scaffold comprising the biopolymer according to claim 1.

4. The cell-harvesting scaffold according to claim 3 where the connection between the biopolymer and the scaffold involves at least two covalent bonds per biopolymer molecule.

5. The cell-harvesting scaffold according to claim 4 where the amino groups or carboxyl groups in the side chains of at least two of the amino acids of peptide D react to form the covalent bonds.

6. The cell-harvesting scaffold according to claim 3 characterised in that the surface thereof is smooth or curved.

7. The cell-harvesting scaffold according to claim 6 characterised by comprising microparticles.

8. A cell-harvesting method comprising the following stages:

(a) functionalisation of a cell culture scaffold, (b) covalently binding the scaffold functionalised in stage (a) to at least two of the amino acids from peptide D present in the biopolymer according to claim 1, (c) bringing a cell suspension into contact with the scaffold obtained in (b), and (d) harvesting the cells adhered to said scaffold.

9. The cell-harvesting method according to claim 8 where the scaffold is functionalised with alkynyl groups, alkene groups, nitrile groups, carbonyl groups or imine groups, and prior to stage (b), the reactive groups in the side chains of at least two of the amino acids from peptide D of the biopolymer are transformed into azide groups.

10. The cell-harvesting method according to claim 8 where the cells adhered to the scaffold are harvested by decreasing the temperature of the cell culture from 37 to 10° C.

11. The cell-harvesting method according to claim 8 where the covalent bond of stage (b) is formed by cycloaddition.

* * * * *

SEQUENCE LISTING

```
<160> NUMBER OF SEQ ID NOS: 19

<210> SEQ ID NO 1
<211> LENGTH: 12
<212> TYPE: PRT
<213> ORGANISM: Homo sapiens

<400> SEQUENCE: 1

Ala Val Thr Gly Arg Gly Asp Ser Pro Ala Ser Ser
1               5                   10

<210> SEQ ID NO 2
<211> LENGTH: 5
<212> TYPE: PRT
<213> ORGANISM: Artificial sequence
<220> FEATURE:
<223> OTHER INFORMATION: Sequence derived from VPGVG from human elastin.

<400> SEQUENCE: 2

Val Pro Gly Ile Gly
1               5

<210> SEQ ID NO 3
<211> LENGTH: 5
<212> TYPE: PRT
<213> ORGANISM: Homo sapiens
```

```
<400> SEQUENCE: 3

Val Pro Gly Val Gly
1               5

<210> SEQ ID NO 4
<211> LENGTH: 6
<212> TYPE: PRT
<213> ORGANISM: Artificial sequence
<220> FEATURE:
<223> OTHER INFORMATION: Preferred embodiment of peptide D.

<400> SEQUENCE: 4

Met Gly Lys Lys Lys Pro
1               5

<210> SEQ ID NO 5
<211> LENGTH: 19
<212> TYPE: PRT
<213> ORGANISM: Homo sapiens

<400> SEQUENCE: 5

Glu Glu Ile Gln Ile Gly His Ile Pro Arg Glu Asp Val Asp Tyr His
1               5                  10                  15

Leu Tyr Pro

<210> SEQ ID NO 6
<211> LENGTH: 6
<212> TYPE: PRT
<213> ORGANISM: Homo sapiens

<400> SEQUENCE: 6

Pro Arg Arg Ala Arg Val
1               5

<210> SEQ ID NO 7
<211> LENGTH: 371
<212> TYPE: PRT
<213> ORGANISM: Artificial sequence
<220> FEATURE:
<223> OTHER INFORMATION: Polymer 1.

<400> SEQUENCE: 7

Met Gly Lys Lys Lys Pro Val Pro Gly Val Gly Val Pro Gly Val Gly
1               5                  10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Ile
65                  70                  75                  80

Gly Val Pro Gly Ile Gly Val Pro Gly Ile Gly Val Pro Gly Ile Gly
                85                  90                  95

Val Pro Gly Ile Gly Val Pro Gly Ile Gly Val Pro Gly Ile Gly Val
            100                 105                 110

Pro Gly Ile Gly Val Pro Gly Ile Gly Val Pro Gly Ile Gly Ala Val
        115                 120                 125

Thr Gly Arg Gly Asp Ser Pro Ala Ser Ser Val Pro Gly Ile Gly Val
    130                 135                 140
```

```
Pro Gly Ile Gly Val Pro Gly Ile Gly Val Pro Gly Ile Gly Val Pro
145                 150                 155                 160
Gly Ile Gly Val Pro Gly Ile Gly Val Pro Gly Ile Gly Val Pro Gly
            165                 170                 175
Ile Gly Val Pro Gly Ile Gly Val Pro Gly Ile Gly Val Pro Gly Ile
        180                 185                 190
Gly Val Pro Gly Ile Gly Val Pro Gly Ile Gly Val Pro Gly Ile Gly
    195                 200                 205
Val Pro Gly Ile Gly Val Pro Gly Ile Gly Val Pro Gly Ile Gly Val
210                 215                 220
Pro Gly Ile Gly Val Pro Gly Ile Gly Val Pro Gly Ile Gly Ala Val
225                 230                 235                 240
Thr Gly Arg Gly Asp Ser Pro Ala Ser Ser Val Pro Gly Ile Gly Val
                245                 250                 255
Pro Gly Ile Gly Val Pro Gly Ile Gly Val Pro Gly Ile Gly Val Pro
            260                 265                 270
Gly Ile Gly Val Pro Gly Ile Gly Val Pro Gly Ile Gly Val Pro Gly
        275                 280                 285
Ile Gly Val Pro Gly Ile Gly Val Pro Gly Ile Gly Val Pro Gly Val
    290                 295                 300
Gly Val Pro Gly Val Gly Val Pro Gly Val Gly Val Pro Gly Val Gly
305                 310                 315                 320
Val Pro Gly Val Gly Val Pro Gly Val Gly Val Pro Gly Val Gly Val
                325                 330                 335
Pro Gly Val Gly Val Pro Gly Val Gly Val Pro Gly Val Gly Val Pro
            340                 345                 350
Gly Val Gly Val Pro Gly Val Gly Val Pro Gly Val Gly Val Pro Gly
        355                 360                 365
Val Gly Val
    370

<210> SEQ ID NO 8
<211> LENGTH: 1113
<212> TYPE: DNA
<213> ORGANISM: Artificial sequence
<220> FEATURE:
<223> OTHER INFORMATION: Coding sequence for polymer 1.

<400> SEQUENCE: 8
atgggtaaaa aaaagccggt accgggcgtg ggcgttccag gcgtgggtgt tccgggtgtg      60
ggcgttccgg gtgtgggtgt tcccggtgtc ggggttcctg gggtaggagt ccccggagtc     120
ggtgttccag gggtcggtgt tcctggcgtg ggtgttccgg gtgtgggcgt tccgggcgtg     180
ggtgttccgg gtgtgggcgt tccaggcgtg ggtgttccgg gtgtgggcgt accgggcatc     240
ggtgttccgg gcattggtgt gccgggcatc ggtgttccgg gcattggtgt gccgggcatc     300
ggtgtgccag gcattggtgt gccgggcatc ggtgttccgg gcattggtgt gccgggcatc     360
ggtgtgccag gcattggtgc agtaaccggt cgtggggatt ctcctgcgtc cagcgtcccg     420
ggcatcggtg ttccgggcat tggtgtgccg ggcatcggtg ttccgggcat tggtgtgccg     480
ggcatcggtg tgccaggcat tggtgtgccg ggcatcggtg ttcccggcat tggtgtgcca     540
ggcatcggtg tgccgggcat tggtgtaccg ggcatcggtg ttcccgggcat tggtgtgccg     600 ggcatcggtg ttcccgggcat tggtgtgccg ggcatcggtg tgccaggcat tggtgtgccg     660
ggcatcggtg ttcccgggcat tggtgtgccg ggcatcggtg tgccaggcat tggtgcagta     720
```

```
accggtcgtg gggattctcc tgcgtccagc gtcccgggca tcggtgttcc gggcattggt    780
gtgccgggca tcggtgttcc gggcattggt gtgccgggca tcggtgtgcc aggcattggt    840
gtgccgggca tcggtgttcc gggcattggt gtgccaggca tcggtgtgcc ggcattggt     900 gtaccgggcg tgggcgttcc aggcgtgggt gttccgggtg tgggcgttcc gggtgtgggt    960
gttcccggtg tcggggttcc tggggtagga gtccccggag tcggtgttcc aggggtcggt   1020
gttcctggcg tgggtgttcc gggtgtgggc gttccgggcg tgggtgttcc gggtgtgggc   1080
gttccaggcg tgggtgttcc gggtgtgggc gta                                1113
```

<210> SEQ ID NO 9
<211> LENGTH: 371
<212> TYPE: PRT
<213> ORGANISM: Artificial sequence
<220> FEATURE:
<223> OTHER INFORMATION: Polymer 2.

<400> SEQUENCE: 9

```
Met Gly Lys Lys Lys Pro Val Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Ile
65                  70                  75                  80

Gly Val Pro Gly Ile Gly Val Pro Gly Ile Gly Val Pro Gly Ile Gly
                85                  90                  95

Val Pro Gly Ile Gly Val Pro Gly Ile Gly Val Pro Gly Ile Gly Val
            100                 105                 110

Pro Gly Ile Gly Val Pro Gly Ile Gly Val Pro Gly Ile Gly Ala Val
        115                 120                 125

Thr Gly Arg Asp Gly Ser Pro Ala Ser Ser Val Pro Gly Ile Gly Val
    130                 135                 140

Pro Gly Ile Gly Val Pro Gly Ile Gly Val Pro Gly Ile Gly Val Pro
145                 150                 155                 160

Gly Ile Gly Val Pro Gly Ile Gly Val Pro Gly Ile Gly Val Pro Gly
                165                 170                 175

Ile Gly Val Pro Gly Ile Gly Val Pro Gly Ile Gly Val Pro Gly Ile
            180                 185                 190

Gly Val Pro Gly Ile Gly Val Pro Gly Ile Gly Val Pro Gly Ile Gly
        195                 200                 205

Val Pro Gly Ile Gly Val Pro Gly Ile Gly Val Pro Gly Ile Gly Val
    210                 215                 220

Pro Gly Ile Gly Val Pro Gly Ile Gly Val Pro Gly Ile Gly Ala Val
225                 230                 235                 240

Thr Gly Arg Asp Gly Ser Pro Ala Ser Ser Val Pro Gly Ile Gly Val
                245                 250                 255

Pro Gly Ile Gly Val Pro Gly Ile Gly Val Pro Gly Ile Gly Val Pro
            260                 265                 270

Gly Ile Gly Val Pro Gly Ile Gly Val Pro Gly Ile Gly Val Pro Gly
        275                 280                 285
```

```
Ile Gly Val Pro Gly Ile Gly Val Pro Gly Ile Gly Val Pro Gly Val
        290                 295                 300

Gly Val Pro Gly Val Gly Val Pro Gly Val Gly Val Pro Gly Val Gly
305                 310                 315                 320

Val Pro Gly Val Gly Val Pro Gly Val Gly Val Pro Gly Val Gly Val
            325                 330                 335

Pro Gly Val Gly Val Pro Gly Val Gly Val Pro Gly Val Gly Val Pro
        340                 345                 350

Gly Val Gly Val Pro Gly Val Gly Val Pro Gly Val Gly Val Pro Gly
            355                 360                 365

Val Gly Val
    370

<210> SEQ ID NO 10
<211> LENGTH: 1113
<212> TYPE: DNA
<213> ORGANISM: Artificial sequence
<220> FEATURE:
<223> OTHER INFORMATION: Coding sequence for polymer 2.

<400> SEQUENCE: 10
atgggtaaaa aaaagccggt accgggcgtg ggcgttccag gcgtgggtgt tccgggtgtg      60
ggcgttccgg gtgtgggtgt tcccggtgtc ggggttcctg gggtaggagt ccccggagtc     120
ggtgttccag gggtcggtgt tcctggcgtg ggtgttccgg gtgtgggcgt tccgggcgtg     180
ggtgttccgg gtgtgggcgt tccaggcgtg ggtgttccgg gtgtgggcgt accgggcatc     240
ggtgttccgg gcattggtgt gccgggcatc ggtgttccgg gcattggtgt gccgggcatc     300
ggtgtgccag gcattggtgt gccgggcatc ggtgttccgg gcattggtgt gccgggcatc     360
ggtgtgccag gcattggtgc agtaaccggt cgtgatgggt ctcctgcgtc cagcgtcccg     420
ggcatcggtg ttccgggcat tggtgtgccg ggcatcggtg ttccgggcat tggtgtgccg     480
ggcatcggtg tgccaggcat tggtgtgccg ggcatcggtg ttccgggcat tggtgtgcca     540
ggcatcggtg tgccgggcat tggtgtaccg ggcatcggtg ttccgggcat tggtgtgccg     600
ggcatcggtg ttccgggcat tggtgtgccg ggcatcggtg tgccaggcat tggtgtgccg     660
ggcatcggtg ttccgggcat tggtgtgccg ggcatcggtg tgccaggcat tggtgcagta     720
accggtcgtg atgggtctcc tgcgtccagc gtcccgggca tcggtgttcc gggcattggt     780
gtgccgggca tcggtgttcc gggcattggt gtgccgggca tcggtgtgcc aggcattggt     840
gtgccgggca tcggtgttcc gggcattggt gtgccaggca tcggtgtgcc gggcattggt     900
gtaccgggcg tgggcgttcc aggcgtgggt gttccgggtg tgggcgttcc gggtgtgggt     960
gttccggtgt cggggttcc tggggtagga gtccccggag tcggtgttcc aggggtcggt    1020
gttcctggcg tgggtgttcc gggtgtgggc gttccgggcg tgggtgttcc gggtgtgggc    1080
gttccaggcg tgggtgttcc gggtgtgggc gta                                 1113

<210> SEQ ID NO 11
<211> LENGTH: 427
<212> TYPE: PRT
<213> ORGANISM: Artificial sequence
<220> FEATURE:
<223> OTHER INFORMATION: Polymer 3.

<400> SEQUENCE: 11

Met Gly Lys Lys Lys Pro Val Pro Gly Val Gly Val Pro Gly Val Gly
1               5                   10                  15
```

```
Val Pro Gly Val Gly Val Pro Gly Val Gly Val
         20                  25                  30
Pro Gly Val Gly Val Pro Gly Val Gly Val Pro
         35                  40                  45
Gly Val Gly Val Pro Gly Val Gly Val Pro Gly
         50                  55                  60
Val Gly Val Pro Gly Val Gly Val Pro Gly Val
65                   70                  75                  80
Gly Val Pro Gly Val Gly Val Pro Gly Val Gly
             85                  90                  95
Val Pro Gly Val Gly Val Pro Gly Val Gly Val
         100                 105                 110
Pro Gly Val Gly Val Pro Gly Val Gly Val Pro
         115                 120                 125
Gly Val Gly Val Pro Gly Val Gly Val Pro Gly
         130                 135                 140
Val Gly Val Pro Gly Val Gly Val Pro Gly Val
145                  150                 155                 160
Gly Val Pro Gly Val Gly Val Pro Gly Val Gly
             165                 170                 175
Val Pro Gly Val Gly Val Pro Gly Val Gly Val
         180                 185                 190
Pro Gly Val Gly Val Pro Gly Val Gly Val Pro
         195                 200                 205
Gly Val Gly Val Pro Gly Val Gly Val Pro Gly
         210                 215                 220
Val Gly Val Pro Gly Val Gly Val Pro Gly Val
225                  230                 235                 240
Gly Val Pro Gly Val Gly Val Pro Gly Val Gly
             245                 250                 255
Val Pro Gly Val Gly Val Pro Gly Val Gly Val
         260                 265                 270
Pro Gly Val Gly Val Pro Gly Val Gly Val Pro
         275                 280                 285
Gly Val Gly Val Pro Gly Val Gly Val Pro Gly
         290                 295                 300
Val Gly Val Pro Gly Val Gly Val Pro Gly Val
305                  310                 315                 320
Gly Val Pro Gly Val Gly Val Pro Gly Val Gly
             325                 330                 335
Val Pro Gly Val Gly Val Pro Gly Val Gly Val
         340                 345                 350
Pro Gly Val Gly Val Pro Gly Val Gly Val Pro
         355                 360                 365
Gly Val Gly Val Pro Gly Val Gly Val Pro Gly
         370                 375                 380
Val Gly Val Pro Gly Val Gly Val Pro Gly Val
385                  390                 395                 400
Gly Val Pro Gly Val Gly Val Pro Gly Val Gly
             405                 410                 415
Val Pro Gly Val Gly Val Pro Gly Val Gly Val
         420                 425
```

<210> SEQ ID NO 12
<211> LENGTH: 1281
<212> TYPE: DNA
<213> ORGANISM: Artificial sequence
<220> FEATURE:
<223> OTHER INFORMATION: Coding sequence for polymer 3.

<400> SEQUENCE: 12

```
atgggtaaaa aaaagccggt accgggcgtg ggcgttccag gcgtgggtgt tccgggtgtg      60
ggcgttccgg gtgtgggtgt tcccggtgtc ggggttcctg gggtaggagt ccccggagtc     120
ggtgttccag gggtcggtgt tcctggcgtg ggtgttccgg gtgtgggcgt tccgggcgtg     180
ggtgttccgg gtgtgggcgt tccaggcgtg ggtgttccgg gtgtgggcgt accgggcgtg     240
ggcgttccag gcgtgggtgt tccgggtgtg ggcgttccgg gtgtgggtgt tcccggtgtc     300
ggggttcctg gggtaggagt ccccggagtc ggtgttccag gggtcggtgt tcctggcgtg     360
ggtgttccgg gtgtgggcgt tccgggcgtg ggtgttccgg gtgtgggcgt tccaggcgtg     420
ggtgttccgg gtgtgggcgt accgggcgtg ggcgttccag gcgtgggtgt tccgggtgtg     480
ggcgttccgg gtgtgggtgt tcccggtgtc ggggttcctg gggtaggagt ccccggagtc     540
ggtgttccag gggtcggtgt tcctggcgtg ggtgttccgg gtgtgggcgt tccgggcgtg     600
ggtgttccgg gtgtgggcgt tccaggcgtg ggtgttccgg gtgtgggcgt accgggcgtg     660
ggcgttccag gcgtgggtgt tccgggtgtg ggcgttccgg gtgtgggtgt tcccggtgtc     720
ggggttcctg gggtaggagt ccccggagtc ggtgttccag gggtcggtgt tcctggcgtg     780
ggtgttccgg gtgtgggcgt tccgggcgtg ggtgttccgg gtgtgggcgt tccaggcgtg     840
ggtgttccgg gtgtgggcgt accgggcgtg ggcgttccag gcgtgggtgt tccgggtgtg     900
ggcgttccgg gtgtgggtgt tcccggtgtc ggggttcctg gggtaggagt ccccggagtc     960
ggtgttccag gggtcggtgt tcctggcgtg ggtgttccgg gtgtgggcgt tccgggcgtg    1020
ggtgttccgg gtgtgggcgt tccaggcgtg ggtgttccgg gtgtgggcgt accgggcgtg    1080
ggcgttccag gcgtgggtgt tccgggtgtg ggcgttccgg gtgtgggtgt tcccggtgtc    1140
ggggttcctg gggtaggagt ccccggagtc ggtgttccag gggtcggtgt tcctggcgtg    1200
ggtgttccgg gtgtgggcgt tccgggcgtg ggtgttccgg gtgtgggcgt tccaggcgtg    1260
ggtgttccgg gtgtgggcgt a                                              1281
```

<210> SEQ ID NO 13
<211> LENGTH: 371
<212> TYPE: PRT
<213> ORGANISM: Artificial sequence
<220> FEATURE:
<223> OTHER INFORMATION: Polymer 4.

<400> SEQUENCE: 13

```
Met Glu Ser Leu Leu Pro Val Pro Gly Val Gly Val Pro Gly Val Gly
1               5                   10                  15

Val Pro Gly Val Gly Val Pro Gly Val Gly Val Pro Gly Val Gly Val
                20                  25                  30

Pro Gly Val Gly Val Pro Gly Val Gly Val Pro Gly Val Gly Val Pro
            35                  40                  45

Gly Val Gly Val Pro Gly Val Gly Val Pro Gly Val Gly Val Pro Gly
        50                  55                  60

Val Gly Val Pro Gly Val Gly Val Pro Gly Val Gly Val Pro Gly Ile
65                  70                  75                  80

Gly Val Pro Gly Ile Gly Val Pro Gly Ile Gly Val Pro Gly Ile Gly
```

```
                85                  90                  95
Val Pro Gly Ile Gly Val Pro Gly Ile Gly Val Pro Gly Ile Gly Val
            100                 105                 110
Pro Gly Ile Gly Val Pro Gly Ile Gly Val Pro Gly Ile Gly Ala Val
            115                 120                 125
Thr Gly Arg Gly Asp Ser Pro Ala Ser Ser Val Pro Gly Ile Gly Val
            130                 135                 140
Pro Gly Ile Gly Val Pro Gly Ile Gly Val Pro Gly Ile Gly Val Pro
145                 150                 155                 160
Gly Ile Gly Val Pro Gly Ile Gly Val Pro Gly Ile Gly Val Pro Gly
                165                 170                 175
Ile Gly Val Pro Gly Ile Gly Val Pro Gly Ile Gly Val Pro Gly Ile
            180                 185                 190
Gly Val Pro Gly Ile Gly Val Pro Gly Ile Gly Val Pro Gly Ile Gly
            195                 200                 205
Val Pro Gly Ile Gly Val Pro Gly Ile Gly Val Pro Gly Ile Gly Val
            210                 215                 220
Pro Gly Ile Gly Val Pro Gly Ile Gly Val Pro Gly Ile Gly Ala Val
225                 230                 235                 240
Thr Gly Arg Gly Asp Ser Pro Ala Ser Ser Val Pro Gly Ile Gly Val
                245                 250                 255
Pro Gly Ile Gly Val Pro Gly Ile Gly Val Pro Gly Ile Gly Val Pro
            260                 265                 270
Gly Ile Gly Val Pro Gly Ile Gly Val Pro Gly Ile Gly Val Pro Gly
            275                 280                 285
Ile Gly Val Pro Gly Ile Gly Val Pro Gly Ile Gly Val Pro Gly Val
            290                 295                 300
Gly Val Pro Gly Val Gly Val Pro Gly Val Gly Val Pro Gly Val Gly
305                 310                 315                 320
Val Pro Gly Val Gly Val Pro Gly Val Gly Val Pro Gly Val Gly Val
                325                 330                 335
Pro Gly Val Gly Val Pro Gly Val Gly Val Pro Gly Val Gly Val Pro
            340                 345                 350
Gly Val Gly Val Pro Gly Val Gly Val Pro Gly Val Gly Val Pro Gly
            355                 360                 365
Val Gly Val
    370

<210> SEQ ID NO 14
<211> LENGTH: 1113
<212> TYPE: DNA
<213> ORGANISM: Artificial sequence
<220> FEATURE:
<223> OTHER INFORMATION: Coding sequence for polymer 4.

<400> SEQUENCE: 14
atggaatccc tgctgccggt accgggcgtg ggcgttccag gcgtgggtgt tccgggtgtg      60
ggcgttccgg gtgtgggtgt tcccggtgtc ggggttcctg ggtaggagt ccccggagtc     120 ggtgttccag gggtcggtgt tcctggcgtg ggtgttccgg gtgtgggcgt tccgggcgtg    180
ggtgttccgg gtgtgggcgt tccaggcgtg ggtgttccgg gtgtgggcgt accgggcatc    240
ggtgttccgg gcattggtgt gccgggcatc ggtgttccgg gcattggtgt gccgggcatc    300
ggtgtgccag gcattggtgt gccgggcatc ggtgttccgg gcattggtgt gccgggcatc    360
ggtgtgccag gcattggtgc agtaaccggt cgtggggatt ctcctgcgtc cagcgtcccg    420
```

```
ggcatcggtg ttccgggcat tggtgtgccg ggcatcggtg ttccgggcat tggtgtgccg      480
ggcatcggtg tgccaggcat tggtgtgccg ggcatcggtg ttccgggcat tggtgtgcca      540
ggcatcggtg tgccgggcat tggtgtaccg ggcatcggtg ttccgggcat tggtgtgccg      600
ggcatcggtg ttccgggcat tggtgtgccg ggcatcggtg tgccaggcat tggtgtgccg      660
ggcatcggtg ttccgggcat tggtgtgccg ggcatcggtg tgccaggcat tggtgcagta      720
accggtcgtg gggattctcc tgcgtccagc gtcccgggca tcggtgttcc ggcattggt       780 gtgccgggca tcggtgttcc gggcattggt gtgccgggca tcggtgtgcc aggcattggt      840
gtgccgggca tcggtgttcc gggcattggt gtgccaggca tcggtgtgcc gggcattggt      900
gtaccgggcg tgggcgttcc aggcgtgggt gttccgggtg tgggcgttcc gggtgtgggt      960
gttcccggtg tcggggttcc tggggtagga gtccccggag tcggtgttcc aggggtcggt     1020
gttcctggcg tgggtgttcc gggtgtgggc gttccgggcg tgggtgttcc gggtgtgggc     1080
gttccaggcg tgggtgttcc gggtgtgggc gta                                  1113

<210> SEQ ID NO 15
<211> LENGTH: 699
<212> TYPE: PRT
<213> ORGANISM: Artificial sequence
<220> FEATURE:
<223> OTHER INFORMATION: Polymer 5.

<400> SEQUENCE: 15

Met Gly Ser Ser His His His His His His Ser Ser Gly Leu Val Pro
1               5                   10                  15

Arg Gly Ser His Met Glu Ser Leu Leu Pro Val Pro Gly Ile Gly Val
            20                  25                  30

Pro Gly Ile Gly Val Pro Gly Lys Gly Val Pro Gly Ile Gly Val Pro
        35                  40                  45

Gly Ile Gly Val Pro Gly Ile Gly Val Pro Gly Ile Gly Val Pro Gly
    50                  55                  60

Lys Gly Val Pro Gly Ile Gly Val Pro Gly Ile Gly Ala Val Thr Gly
65                  70                  75                  80

Arg Gly Asp Ser Pro Ala Ser Ser Val Pro Gly Ile Gly Val Pro Gly
                85                  90                  95

Ile Gly Val Pro Gly Lys Gly Val Pro Gly Ile Gly Val Pro Gly Ile
            100                 105                 110

Gly Val Pro Gly Ile Gly Val Pro Gly Ile Gly Val Pro Gly Lys Gly
        115                 120                 125

Val Pro Gly Ile Gly Val Pro Gly Ile Gly Val Pro Gly Ile Gly Val
    130                 135                 140

Pro Gly Ile Gly Val Pro Gly Lys Gly Val Pro Gly Ile Gly Val Pro
145                 150                 155                 160

Gly Ile Gly Val Pro Gly Ile Gly Val Pro Gly Ile Gly Val Pro Gly
                165                 170                 175

Lys Gly Val Pro Gly Ile Gly Val Pro Gly Ile Gly Ala Val Thr Gly
            180                 185                 190

Arg Gly Asp Ser Pro Ala Ser Ser Val Pro Gly Ile Gly Val Pro Gly
        195                 200                 205

Ile Gly Val Pro Gly Lys Gly Val Pro Gly Ile Gly Val Pro Gly Ile
    210                 215                 220

Gly Val Pro Gly Ile Gly Val Pro Gly Ile Gly Val Pro Gly Lys Gly
225                 230                 235                 240
```

```
Val Pro Gly Ile Gly Val Pro Gly Ile Gly Val
            245                 250             255

Pro Gly Ile Gly Val Pro Gly Lys Gly Val Pro Gly Ile Gly Val Pro
                260                 265                 270

Gly Ile Gly Val Pro Gly Ile Gly Val Pro Gly Ile Gly Val Pro Gly
            275                 280                 285

Lys Gly Val Pro Gly Ile Gly Val Pro Gly Ile Gly Ala Val Thr Gly
            290                 295                 300

Arg Gly Asp Ser Pro Ala Ser Ser Val Pro Gly Ile Gly Val Pro Gly
305                 310                 315                 320

Ile Gly Val Pro Gly Lys Gly Val Pro Gly Ile Gly Val Pro Gly Ile
            325                 330                 335

Gly Val Pro Gly Ile Gly Val Pro Gly Ile Gly Val Pro Gly Lys Gly
            340                 345                 350

Val Pro Gly Ile Gly Val Pro Gly Ile Gly Val Pro Gly Ile Gly Val
            355                 360                 365

Pro Gly Ile Gly Val Pro Gly Lys Gly Val Pro Gly Ile Gly Val Pro
            370                 375                 380

Gly Ile Gly Val Pro Gly Ile Gly Val Pro Gly Ile Gly Val Pro Gly
385                 390                 395                 400

Lys Gly Val Pro Gly Ile Gly Val Pro Gly Ile Gly Ala Val Thr Gly
            405                 410                 415

Arg Gly Asp Ser Pro Ala Ser Ser Val Pro Gly Ile Gly Val Pro Gly
            420                 425                 430

Ile Gly Val Pro Gly Lys Gly Val Pro Gly Ile Gly Val Pro Gly Ile
            435                 440                 445

Gly Val Pro Gly Ile Gly Val Pro Gly Ile Gly Val Pro Gly Lys Gly
            450                 455                 460

Val Pro Gly Ile Gly Val Pro Gly Ile Gly Val Pro Gly Ile Gly Val
465                 470                 475                 480

Pro Gly Ile Gly Val Pro Gly Lys Gly Val Pro Gly Ile Gly Val Pro
            485                 490                 495

Gly Ile Gly Val Pro Gly Ile Gly Val Pro Gly Ile Gly Val Pro Gly
            500                 505                 510

Lys Gly Val Pro Gly Ile Gly Val Pro Gly Ile Gly Ala Val Thr Gly
            515                 520                 525

Arg Gly Asp Ser Pro Ala Ser Ser Val Pro Gly Ile Gly Val Pro Gly
            530                 535                 540

Ile Gly Val Pro Gly Lys Gly Val Pro Gly Ile Gly Val Pro Gly Ile
545                 550                 555                 560

Gly Val Pro Gly Ile Gly Val Pro Gly Ile Gly Val Pro Gly Lys Gly
            565                 570                 575

Val Pro Gly Ile Gly Val Pro Gly Ile Gly Val Pro Gly Ile Gly Val
            580                 585                 590

Pro Gly Ile Gly Val Pro Gly Lys Gly Val Pro Gly Ile Gly Val Pro
            595                 600                 605

Gly Ile Gly Val Pro Gly Ile Gly Val Pro Gly Ile Gly Val Pro Gly
            610                 615                 620

Lys Gly Val Pro Gly Ile Gly Val Pro Gly Ile Gly Ala Val Thr Gly
625                 630                 635                 640

Arg Gly Asp Ser Pro Ala Ser Ser Val Pro Gly Ile Gly Val Pro Gly
            645                 650                 655
```

```
Ile Gly Val Pro Gly Lys Gly Val Pro Gly Ile Gly Val Pro Gly Ile
            660                 665                 670

Gly Val Pro Gly Ile Gly Val Pro Gly Ile Gly Val Pro Gly Lys Gly
        675                 680                 685

Val Pro Gly Ile Gly Val Pro Gly Ile Gly Val
    690                 695

<210> SEQ ID NO 16
<211> LENGTH: 4
<212> TYPE: PRT
<213> ORGANISM: Homo sapiens

<400> SEQUENCE: 16

Arg Glu Asp Val
1

<210> SEQ ID NO 17
<211> LENGTH: 4
<212> TYPE: PRT
<213> ORGANISM: Homo sapiens

<400> SEQUENCE: 17

Asp Gly Glu Ala
1

<210> SEQ ID NO 18
<211> LENGTH: 5
<212> TYPE: PRT
<213> ORGANISM: Homo sapiens

<400> SEQUENCE: 18

Tyr Ile Gly Ser Arg
1               5

<210> SEQ ID NO 19
<211> LENGTH: 9
<212> TYPE: PRT
<213> ORGANISM: Homo sapiens

<400> SEQUENCE: 19

Gln Ala Ala Ser Ile Lys Val Ala Val
1               5
```